(12) United States Patent
Tavazza et al.

(10) Patent No.: US 7,732,665 B2
(45) Date of Patent: Jun. 8, 2010

(54) METHOD FOR THE PREPARATION OF TRANSGENIC PLANTS CHARACTERISED BY GEMINIVIRUS LASTING RESISTANCE

(75) Inventors: Mario Tavazza, Rome (IT); Raffaela Tavazza, Rome (IT); Alessandra Lucioli, Rome (IT); Angela Brunetti, Rome (IT); Alessandra Berardi, Rome (IT); Emanuela Noris, Rome (IT); Gian Paolo Accotto, Rome (IT)

(73) Assignees: Consiglio Nazionale delle Ricerche, Rome (IT), part interest; ENEA — Ente per le Nuove Tecnologie, l'Energia e l'Ambiente, Rome (IT), part interest ( * ) Notice: Subject to any disclaimer, the term of this patent is extended or adjusted under 35 U.S.C. 154(b) by 541 days.

(21) Appl. No.: 10/557,288

(22) PCT Filed: May 19, 2004

(86) PCT No.: PCT/IT2004/000287

§ 371 (c)(1),
(2), (4) Date: Feb. 27, 2006

(87) PCT Pub. No.: WO2004/101798

PCT Pub. Date: Nov. 25, 2004

(65) Prior Publication Data

US 2006/0206959 A1     Sep. 14, 2006

(30) Foreign Application Priority Data

May 19, 2003     (IT) .......................... RM2003A0242

(51) Int. Cl.
*A01H 1/00*     (2006.01)
*C12N 15/82*    (2006.01)
*C12N 15/87*    (2006.01)

(52) U.S. Cl. ........................ 800/288; 800/278; 800/279

(58) Field of Classification Search ....................... None
See application file for complete search history.

(56) References Cited

U.S. PATENT DOCUMENTS

2005/0125862 A1*    6/2005    Polston et al. .............. 800/301

FOREIGN PATENT DOCUMENTS

WO          WO 00/43520          7/2000

OTHER PUBLICATIONS van Wezel et al 2002, MPMI 15:203-208.*
Vanderschuren et al, 2007 Plant Biotechnology Journal 207-220.*
Lazar et al. 1988, Mol. Cell. Biol. 8:1247-1252.*
Hill et al 1998, Biochem. Biophys. Res. Comm. 244:573-577.*
Guo et al. 2004, Proc. Natl. Acad. Sci. USA 101: 9205-9210.*
Brunetti Angela et al:, "Transgenically expressed T-Rep of tomato yellow leaf curl sardinia virus acts as a trans-dominant-negative mutant, inhibiting viral transcription and replication", Journal of Virology, vol. 75, No. 22, Nov. 2001, pp. 10573-10581, XP002300782, ISSN: 0022-538X, the whole document.
Noris E et al:, Resistance to tomato yellow leaf curl geminivirus in Nicotiana benthamiana plants transformed with a truncated viral C1 gene, Virology, Academic Press, Orlando, US, vol. 224, No. 1, 1996, pp. 130-138, XP002142359, ISSN: 0042-6822, the whole document.

* cited by examiner

*Primary Examiner*—Anne Kubelik
*Assistant Examiner*—Li Zheng
(74) *Attorney, Agent, or Firm*—Young & Thompson

(57) ABSTRACT

The present invention relates to a method for the preparation of transgenic plants, tissues or plant cells thereof having long-lasting resistant to the geminiviruses by a) "identification" or "selection" of a viral gene sequence encoding an amino acid sequence able to confer resistance against geminiviruses; b) mutagenesis or "choice" of the viral gene sequence so as to make it an ineffective target of the posttrascriptional silencing induced by infecting geminivirus; and c) insertion of the geminivirus mutated or chosen gene sequence obtained in step b) through a construct as described previously, in the plant, tissue or plant cell thereof.

17 Claims, 16 Drawing Sheets

Fig. 1

100  50    1    2    C
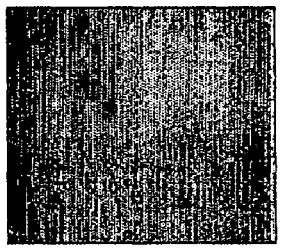 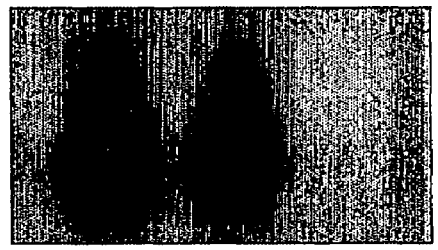 probe A
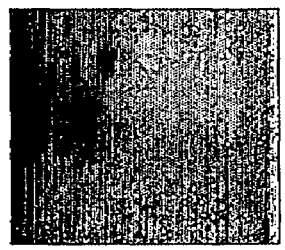 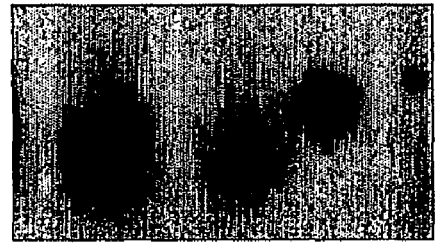 probe B
Fig. 7

SEQ ID No 8

GGATCCCCctggatactttgagtgtcccccgattcagaac 40
gacagcaaaaatgccaagatcaggtcgttttagtatcaag 80
gctaaaaattatttccttacatatcccaaatgtgatttaa 120
caaaagaaaatgcactttcccaataacaaacctacaaac 160
acccacaaacaaattattcatcaaatttgcagagaacta 200
catgaaaatggggaacctcatctccatatttgatccaat 240
tcgaaggaaaatacaattgtaccaatcaacgattcttcga 280
cctggtatccccaaccaggtcagcacatttccatccgaac 320
attcagggagctaaatcgagctccgacgtcaagtcctata 360
tcgacaaggacggagatgttcttgaatggggtactttcca 400
gatcgacggacgatctgctaggggaggacaacagacagcc 440
tGAATTC 447

Fig. 8

Fig. 14
Fig. 15

METHOD FOR THE PREPARATION OF TRANSGENIC PLANTS CHARACTERISED BY GEMINIVIRUS LASTING RESISTANCE

This is a 371 National Stage application of International application no. PCT/IT04/00287, filed May 19, 2004, which claims priority to Italian application no. RM2003A000242, filed May 19, 2003. The entire contents of the above-referenced applications are hereby incorporated by reference in their entirety.

The present invention relates to a method for the preparation of transgenic plants lasting resistant to geminiviruses.

More particularly the invention concerns a method for the preparation of transgenic plants lasting resistant to geminiviruses, wherein the transgene consists of a polynucleotide sequence, derived from the pathogen, suitably modified in order to result in an ineffective target of the post-trascriptional gene silencing induced by geminiviruses.

BACKGROUND OF THE INVENTION

It is known that geminiviruses are a wide and diversified class of plant viruses that infect several plants of agronomic interest causing serious harvest losses. Such viruses are characterised by virions consisting of two geminate icosahedric particles. Their genome, consisting of one or two circular single-stranded DNA molecules (ssDNA), replicates in the nucleus of infected cells through double stranded intermediates (Hanley-Bowdoin et al., 1999).

The Geminiviridae family is divided in four genera named Mastrevirus, Begomovirus, Curtovirus and Topocuvirus based on the insect vector, the host spectrum and the genome structure (Briddon et al., 1985; Fauquet et al., 2003).

A serious disease of the tomato plant, transmitted by the whitefly *Bemisia tabaci*, is from a long time known as "tomato yellow leaf curl" in the areas of the Middle East, Asian South East and Africa, (Czosnek et al., 1997). This disease, that can cause harvest losses of 100% (Picò et al., 1996; Czosnek et al., 1997), successively spread both throughout the Western Mediterranean, reaching Sardinia, Sicily and Spain (Czosnek et al., 1997), and America (Polston et al., 1997).

Recently the agents of the disease have been identified and isolated, being viruses belonging to the Geminiviridae family, genera Begomovirus. Phylogenetic studies have highlighted the presence of different viral species related to different geographical origins of the Begomovirus: Asia, Africa and America (Czosnek et al., 1997).

The genoma of the Tomato yellow leaf curl Sardinia virus (TYLCSV) species, is monopartite (Kheyr-Pour et al., 1991). The DNA is transcribed bidirectionally and contains six open reading frame (ORF), two on the viral strand (V): V1 and V2, and four on the complementary strand (C): C1, C2, C3 and C4, as shown in FIG. 1. Between the C1 and V2 ORFs there is a non-coding region named intergenic region (IR) analogous to that present in the genome of all Geminiviridae. The genomic organization of TYLCSV is structurally similar to that of the bipartite Begomoviruses component A such as the tomato golden mosaic virus (TGMV) and the African cassava virus (ACMV). In the case of bipartite Begomoviruses the nomenclature of the ORFs present on the component A of the complementary strand is: AL1 or AC1, AL2 or AC2, AL3 or AC3, AL4 or AC4, while on the viral strand AR1 or AV1, AR2 or AV2; on the complementary strand of the component B is: BL1 or BC1 and on the viral strand BR1 or BV1.

Strategies used until now in order to control the infection of the geminiviruses transmitted by the *Bemisia tabaci* are based on the use of expensive fine mesh nets (for the cultivation of fresh-market tomato) and particularly on repeated insecticide treatments (cultivations of both fresh-market and processing tomato). Such strategies result in an increase of the production expenses and represent a serious danger for the health of the agricultural operators and consumer. Furthermore the onset of *Bemisia tabaci* populations resistant to the insecticide imidacloprid has been already reported (Cahill et al., 1996; Williams et al., 1996).

The development of resistant cultivated species represents the most practical and economic way to control viral infections. Classical breeding programs for introducing resistance to geminiviruses that cause the tomato yellow leaf curl were based on the transfer of resistance genes from wild species of *Lycopersicon* to species of cultivated tomato. Thereby lines with variable levels of resistance to TYLCSV have been obtained and commercialized, the best lines showing reduced symptoms and low viral replication. However plants with low and mean levels of resistance represent a potential receptacle for further infections.

Another important aspect to be considered is that the agronomic characteristics of the lines obtained are not always optimal and however reflects those of the genotype of cultivated tomato used in breeding programs.

A tomato line immune to the viruses causing the tomato yellow leaf curl disease, namely, with neither symptoms nor viral DNA replication has not been released yet.

With the advent of genetic engineering new perspectives were opened up for the introduction of resistance characters against plant viruses. Most strategies are based on the introduction and expression of pathogen-derived sequences in the plant of interest, Pathogen Derived Resistance (PDR) (Sanford & Johnson, 1985; Abel et al., 1986; Tavazza and Lucioli, 1993).

Although such strategies have been successfully applied for the introduction of resistance characters to plant viruses with RNA genome (Beachy, 1997), in the case of geminiviruses, with a DNA genome, the expression of pathogen-derived sequences has produced plants with no lasting resistance and/or tolerance.

The mechanisms that induce virus resistance achieved through the expression of pathogen-derived sequences can be grouped in two wide classes:

a) resistance mediated by the expression of a pathogen protein such as, for instance, the expression of a dominant negative mutant;

b) resistance mediated by the post-transcriptional gene silencing (Baulcombe, 1996; Beachy, 1997; Zaitlin and Palukaitis, 2000).

The post-trascriptional gene silencing is a ubiquitary process in eukaryotes, involving the degradation of specific RNAs following the formation of double strand RNA (dsRNA) molecules having sequences homologous to the target RNA.

Although there may be different contexts able to induce the production of dsRNA homologous to the transgene (transcription of aberrant transgenic RNAs, presence in the transgenic RNA of sufficiently long inverted and repeated sequences, integration of the transgene in the plant genome in inverted and repeated multiple copies), once the dsRNA is produced, the latter is recognised and degraded in short molecules of dsRNA of about 21-26 nucleotides, referred to as siRNA.

The siRNAs are then integrated in a multiprotein complex named RISC, that is able to degrade all RNAs having sequence homology with the siRNAs. The latter ones represent therefore the determining factors of RNA silencing specificity and their presence related to a determined sequence establishes univocally that this RNA sequence is post-transcriptionally silenced.

Therefore, transgenic plants post-transcriptionally silenced for sequences derived from viral RNA genome, are resistant to the homologous virus and to viruses with nucleotide sequences closely related to the transgene.

The transgene silencing can be also induced following virus infection.

In fact, viral replication is able to induce silencing of a transgene, initially not silenced, if the nucleotide sequence of the transgene is homologous to a portion of the infecting virus genome. The activation of the silencing mechanism involves the specific degradation of the RNA molecules having sequence homology with the inducer RNA.

As direct consequence, the silencing activation by the virus is associated with a degradation of both transgenic mRNA sequences homologous to the virus and viral genome. This results in the host recovery after an initial infectious step, so that the new vegetative part is proved to be virus free. A peculiar characteristic of the plant tissues that develop subsequently to the recovery phenomenon is that they are highly resistant to a following infection by the same virus.

The resistance mediated by post-transcriptional gene silencing, since based on recognition at the nucleotidic level, confers resistance only against viral isolates closely homologous to the virus genome from which the transgene was derived. Instead, strategies based on the expression of a pathogen protein normally produce plants resistant also to viral strains or isolates not-closely related from a nucleotide point of view.

It is also been shown that the transgene silencing is influenced by the temperature, being inactive at temperatures below 15° C. (Szittya et al., 2003). Therefore plants exposed in field conditions at temperature range below 15° C. can lose the silencing-mediated resistance.

It must be borne in mind that, although from several years transgenic plants resistant to RNA genome viruses have been achieved through mechanisms based on transgene silencing, so far it is not reported that such strategy can be successfully applied to the geminiviruses (DNA genome-viruses).

It's clear that the best strategy in order to obtain plants resistant to a wide spectrum of geminiviruses is the one in which the interfering product is the protein. It is clear that the width of the resistance spectrum increases the agronomic and commercial value of the produced plant.

Thereby the expression in transgenic plants of dysfunctional variants of geminivirus replicative Rep protein has been used in order to obtain plants with greater levels of resistance or immunity against the geminiviruses.

It's known in literature that the expression of a truncated replicative Rep protein (Rep-210) of TYLCSV is able to confer resistance against viral infection, although such resistance is not lasting because the virus is able to overcome it over time.

In tables 1 and 2 are shown the results of the analysis of the resistance of TYLCSV-agroinoculated Rep-210 expressing transgenic plants of Tomato 47×wt (Brunetti et al. 1997) and of *N. benthamiana* line 102.22 (Noris et al. 1996) respectively.

TABLE 1

| *Lycopersicon esculentum* | Time (weeks) | N° infected plants/inoculated plants | % infected plants/inoculated plants |
|---|---|---|---|
| Rep-210 | 4 | 0/13 | 0 |
| | 9 | 2/13 | 15 |
| | 18 | 5/13 | 38 |
| Wild-type | 4 | 6/6 | 100 |

TABLE 2

| *Nicotiana benthamiana* | Time (weeks) | N° infected plants/inoculated plants | % infected plants/inoculated plants |
|---|---|---|---|
| Rep-210 | 2 | 4/21 | 19 |
| | 3 | 11/21 | 52 |
| | 4 | 18/21 | 86 |
| Wild-type | 2 | 6/6 | 100 |

From the results reported in tables 1 and 2, it can be clearly inferred that the resistance against TYLCSV mediated by the transgenic expression of a pathogen-derived sequence, is overcome with time.

Similarly, also the resistance induced by the transgenic expression of a dominant negative mutant of Rep of the bipartite geminivirus "African Cassava Mosaic Virus" is overcome with time (Sangaré et al., 1999).

Another example is represented by the transgenic expression of the TYLCV capsid protein in a tomato interspecific hybrid (*Lycopersicon esculentum* X *L. pennellii*) which confers a partial resistance against viral infection (Kunik et al., 1994). Even in this case the resistance mediated by the expression of the capsid protein is not long lasting and it results to be poorly useful from an agronomic point of view.

In the light of the above, is clear the need to have new methods that would allow to use successfully the polynucleotide sequences derived from the geminiviruses in order to obtain long lasting resistant plants against geminiviruses.

The authors of the present invention have now prepared polynucleotide sequences encoding pathogen-derived viral proteins and able to confer virus resistance to the host, suitably modified in order to be ineffective targets of the virus-induced post-transcriptional gene silencing to obtain transgenic plants with lasting levels of resistance against geminiviruses.

In fact during the experiments the authors show that the overcoming of the resistance, and therefore the difficulty to achieve lasting resistance against geminiviruses, is due to the unexpected abilities of the geminiviruses to silence post-transcriptionally the transgene and to spread in a plant in which the transgene, with sequences homologous to the infecting virus, is post-transcriptionally silenced.

As shown in FIGS. 2 and 3, respectively, both in the transgenic plants of *N. benthamiana* line 102.22 and in the plants of Tomato 47×wt the virus ability to overcome the resistance results from the transgene silencing by the same virus and from the unexpected ability of the virus to spread in a silenced plant.

The TYLCSV ability to spread in a plant in which the transgene Rep-210 is post-transcriptionally silenced, is further circumstantiated as set forth in FIG. 4.

The results show that the transgenic tomato plants 47×10D (Brunetti et al., 1997), post-transcriptionally silenced before agroinoculation, as shown by the absence of the Rep-210 protein and by the concurrent presence of the transgene-homologous siRNAs, are susceptible to the TYLCSV infection as well as the controls.

From the above it results that, contrary to RNA viruses, the geminivirus is not blocked by an active silencing of viral gene sequences. The above said is not limited to the kind of transgenic plant to be used or the way the virus should be inoculated, through agroinfection or *Bemisia tabaci*. In fact, as shown in table 3, using a reduced number of viruliferous *bemisia* per plant, so as to infect between 90% and 100% of the control plants, about 40% of transgenic plants (line 201) whose transgene is post-trascriptionally silenced, are not or late infected, while at a higher inoculum concentration, all the plants challenged with viruliferous insects are infected similarly to the experiments carried out using agroinoculation.

TABLE 3

| Molecular Analysis | | Low concentration of inoculum[a] | | | High concentration of inoculum[b] | |
|---|---|---|---|---|---|---|
| before inoculum | 2[c] | 3 | 6 | 2 | 3 | 6 |
| Transgenic plants | | | | | | |
| Rep-210 siRNAs (No) (Si) | 6/15 | 7/15 | 8/15 | 16/21 | 20/21 | 21/21 |
| Not transgenic | | | | | | |
| Rep-210 siRNAs (No) (No) | 11/12 | 11/12 | 11/12 | 8/8 | 8/8 | 8/8 |

[a]Seven viruliferous insects per plant for 2 days
[b]Thirty-five viruliferous insects per plant for 5 days
[c]Weeks after inoculum Therefore it's important to consider that the viral agroinoculation conditions used for testing the resistance and assessing persistence over time (as shown in FIGS. 2, 3 and 4 and in tables 1 and 2) correspond to high or very high viral pressure conditions. This experimental approach allows to identify transgenic plants with very high resistance levels or immune against the viral infection and therefore of very high commercial value.

Accordingly, the introduction of resistance characters against geminiviruses through the expression of pathogen-derived sequences is limited due to the unexpected ability of the geminiviruses to silence post-trascriptionally the transgene and to spread in the silenced plant.

Furthermore the authors show that the transcripts both of positive (V1 and V2) and negative strand (C1, C2, C3 and C4) of TYLCSV are subjected, during a normal infection on wild-type plants, to the viral post-trascriptional silencing, as shown in FIG. 5. This results in the impossibility to achieve long-term resistance through expression of sequences derived from the same pathogen, unless these are suitably modified in order not to be a target or to be an ineffective target of the virus-induced post-trascriptional gene silencing. Instead, by introducing in the plant genome a sequence suitably mutated or chosen according to the invention it is possible to obtain a long lasting resistance against geminiviruses, unlike that achieved with the known methods.

SUMMARY OF THE INVENTION

Therefore it is an object of the present invention a polynucleotide sequence encoding an amino acid sequence derived from geminiviruses, said polynucleotide sequence being characterised in that it is not a target or it is an ineffective target of the viral post-trascriptional silencing and having:

a) a nucleotide homology lower or equal to 90% with respect to the corresponding gene sequence of the geminiviruses against which a resistance is required, preferably lower or equal to 80%, more preferably lower or equal to 70%;

b) a continuous homology in the RNA transcript, with respect to the corresponding gene sequence of the geminiviruses against which a resistance is required, lower or equal to 17 nucleotides, preferably lower or equal to 8 nucleotides, more preferably lower or equal to 5 nucleotides;

c) a maximum length of the sequence containing a single substitution with respect to the corresponding gene sequence of the geminiviruses no longer than 30 nucleotides, preferably no longer than 20 nucleotides, more preferably equal or lower than 9 nucleotides;

said polynucleotide sequence being able to confer to the whole plants, tissues or plant cells therewith transformed, a lasting resistance against the geminiviruses.

The polynucleotide sequences according to the invention can be wild-type or synthetic or produced by mutagenesis and the geminivirus-derived amino acid sequences encoded by them are wild-type or mutant sequences that interfere with the viral infection.

Therefore the invention includes polynucleotide sequences of geminivirus either suitably changed or wild-type, such as to differ, at the nucleotidic level, with respect to the corresponding genomic sequence of the geminivirus against which it is required to introduce resistance according to the principles above defined and specified in a), b) and c).

Further object of the present invention is a polynucleotide sequence encoding a geminivirus-derived amino acid sequence, said polynucleotide sequence being characterised in that it is not a target or it is an ineffective target of the post-trascriptional silencing and having homology even equal to 100% with respect to the sequence of the geminivirus against which it is required a resistance and being shortened so as to be underrepresented in the siRNAs population with respect to the original sequence, even if maintaining similar interfering abilities.

The gene sequences from which constructing the polynucleotide sequence according to the invention can derive from the geminiviruses such as, Mastrevirus, Curtovirus, Begomovirus, Topocuvirus and particularly can be derived from the species shown in table 4 and their isolates, more particularly from the species of Tomato yellow leaf curl and their isolates shown in table 5.

TABLE 4

| List of geminivirus species | Acronym |
|---|---|
| African cassava mosaic virus | ACMV |
| Bean calico mosaic virus | BcaMV |
| Bean dwarf mosaic virus | BDMV |
| Bean golden mosaic virus | BGMV |
| Bean golden yellow mosaic virus | BGYMV |
| Cabbage leaf curl virus | CaLCuV |
| Chilli leaf curl virus | ChiLCuV |
| Cotton leaf crumple virus | CLCrV |
| Cotton leaf curl Alabad virus | CLCuAV |
| Cotton leaf curl Gezira virus | CLCuGV |
| Cotton leaf curl Kokhran virus | CLCuKV |
| Cotton leaf curl Multan virus | CLCuMV |
| Cotton leaf curl Rajasthan virus | CLCuRV |
| Cowpea golden mosaic virus | CPGMV |
| Cucurbit leaf curl virus | CuLCuV |
| East African cassava mosaic Cameroon virus | EACMCV |
| East African cassava mosaic Malawi virus | EACMMV |
| EastAfrican cassava mosaic virus | EACMV |
| East African cassava mosaic Zanzibar virus | EACMZV |
| Indian cassava mosaic virus | ICMV |
| Ipomea yellow vein virus | IYVV |
| Melon chlorotic leaf curl virus | MCLCuV |
| Mungbean yellow mosaic India virus | MYMIV |

TABLE 4-continued

| List of geminivirus species | Acronym |
| --- | --- |
| Mungbean yellow mosaic virus | MYMV |
| Okra yellow vein mosaic virus | OYVMV |
| Papaya leaf curl virus | PaLCuV |
| Pepper golden mosaic virus | PepGMV |
| Pepper huasteco yellow vein virus | PHYVV |
| Pepper leaf curl Bangladesh virus | PepLCBV |
| Pepper leaf curl virus | PepLCV |
| Potato yellow mosaic Panama virus | PYMPV |
| Potato yellow mosaic Trinidad virus | PYMTV |
| Potato yellow mosaic virus | PYMV |
| South African cassava mosaic virus | SACMV |
| Soybean crinkle leaf virus | SbCLV |
| Squash leaf curl China virus | SLCCNV |
| Squash leaf curl virus | SLCV |
| Squash leaf curl Yunnan virus | SLCYV |
| Squash mild leaf curl virus | SMLCV |
| Squash yellow mild mottle virus | SYMMoV |
| Sri Lankan cassava mosaic virus | SLCMV |
| Sweet potato leaf curl Georgia virus | SPLCGV |
| Sweet potato leaf curl virus | SPLCV |
| Tobacco curly shoot virus | TbCSV |
| Tobacco leaf curl Japan virus | TbLCJV |
| Tobacco leaf curl Kochi virus | TbLCKoV |
| Tobacco leaf curl Yunnan virus | TbLCYNV |
| Tobacco leaf curl Zimbabwe virus | TbLCZV |
| Tomato chlorotic mottle virus | ToCMoV |
| Tomato golden mosaic virus | TGMV |
| Tomato golden mottle virus | ToGMoV |
| Tomato leaf curl Bangalore virus | ToLCBV |
| Tomato leaf curl Bangladesh virus | ToLCBDV |
| Tomato leaf curl Gujarat virus | ToLCGV |
| Tomato leaf curl Karnataka virus | ToLCKV |
| Tomato leaf curl Laos virus | ToLCLV |
| Tomato leaf curl Malaysia virus | ToLCMV |
| Tomato leaf curl New Delhi virus | ToLCNDV |
| Tomato leaf curl Sri Lanka virus | ToLCSLV |
| Tomato leaf curl Taiwan virus | ToLCTWV |
| Tomato leaf curl Vietnam virus | ToLCVV |
| Tomato leaf curl virus | ToLCV |
| Tomato mosaic Havana virus | ToMHV |
| Tomato mottle Taino virus | ToMoTV |
| Tomato mottle virus | ToMoV |
| Tomato rugose mosaic virus | ToRMV |
| Tomato severe leaf curl virus | ToSLCV |
| Tomato severe rugose virus | ToSRV |
| Tomato yellow leaf curl China virus | TYLCCNV |
| Tomato yellow leaf curl Gezira virus | TYLCGV |
| Tomato yellow leaf curl Malaga virus | TYLCMalV |
| Tomato yellow leaf curl Sardinia virus | TYLCSV |
| Tomato yellow leaf curl Thailand virus | TYLCTHV |
| Tomato yellow leaf curl virus | TYLCV |
| Watermelon chlorotic stunt virus | WmCSV |
| Wheat dwarf virus | WDV |
| Maize streak virus | MSV |
| Sugarcane streak virus | SSV |
| Bean yellow dwarf virus | BYDV |
| Tobacco yellow dwarf virus | TYDV |
| Tomato pseudo curly top virus | TPCTV |
| Beet curly top virus | BCTV |

TABLE 5

| Species of tomato yellow leaf curl (Fauquet et al., 2003) | Acronym |
| --- | --- |
| Tomato yellow leaf curl China virus | TYLCCNV |
| Tomato yellow leaf curl China virus AF311734 | TYLCCNV |
| Tomato yellow leaf curl China virus - [Y64] AJ457823 | TYLCCNV-[Y64] |
| Tomato yellow leaf curl China virus - Tb [Y10] AJ319675 | TYLCCNV-Tb[Y10] |
| Tomato yellow leaf curl China virus - Tb [Y11] AJ319676 | TYLCCNV-Tb[Y11] |
| Tomato yellow leaf curl China virus - To [Y25] AJ457985 | TYLCCNV-Tb[Y25] |
| Tomato yellow leaf curl China virus - Tb [Y36] AJ420316 | TYLCCNV-Tb[Y36] |
| Tomato yellow leaf curl China virus - Tb [Y38] AJ420317 | TYLCCNV-Tb[Y38] |
| Tomato yellow leaf curl China virus - Tb [Y5] AJ319674 | TYLCCNV-Tb[Y5] |
| Tomato yellow leaf curl China virus - Tb [Y8] AJ319677 | TYLCCNV-Tb[Y8] |
| Tomato yellow leaf curl Gezira virus | TYLCGV |
| Tomato yellow leaf curl Gezira virus - [1] AY044137 | TYLCGV-[1] |
| Tomato yellow leaf curl Gezira virus - [2] AY044138 | TYLCGV-[2] |
| Tomato yellow leaf curl Gezira virus - [Shambat] AY044139 | TYLCGV-[Sha] |
| Tomato yellow leaf curl Malaga virus | TYLCMalV |
| Tomato yellow leaf curl Malaga virus AF271234 | TYLCMalV |
| Tomato yellow leaf curl Sardinia virus | TYLCSV |
| Tomato yellow leaf curl Sardinia virus X61153 | TYLCSV |
| Tomato yellow leaf curl Sardinia virus -Spain [1] Z25751 | TYLCSV-ES[1] |
| Tomato yellow leaf curl Sardinia virus -Spain [2] L27708 | TYLCSV-ES[2] |
| Tomato yellow leaf curl Sardinia virus Sicily Z28390 | TYLCSV-Sic |
| Tomato yellow leaf curl Thailand virus | TYLCTHV |
| Tomato yellow leaf curl Thailand virus - [1] X63015, X63016 | TYLCTHV-[1] |
| Tomato yellow leaf curl Thailand virus - [2] AF141922, AF141897 | TYLCTHV-[2] |
| Tomato yellow leaf curl Thailand virus - [Myanmar] AF206674 | TYLCTHV-[MM] |
| Tomato yellow leaf curl Thailand virus - [Y72] AJ495812 | TYLCTHV-[Y72] |
| Tomato yellow leaf curl virus | TYLCV |
| Tomato yellow leaf curl virus X15656 | TYLCV |
| Tomato yellow leaf curl virus - [Almeria] AJ489258 | TYLCV-[Alm] |
| Tomato yellow leaf curl virus - [Aichi] AB014347 | TYLCV-[Aic] |
| Tomato yellow leaf curl virus - [Cuba] AJ223505 | TYLCV-[CU] |
| Tomato yellow leaf curl virus - [Dominican Republic] AF024715 | TYLCV-[DO] |
| Tomato yellow leaf curl virus - [Portugal] AF105975 | TYLCV-[PT] |

TABLE 5-continued

| Species of tomato yellow leaf curl (Fauquet et al., 2003) | Acronym |
|---|---|
| Tomato yellow leaf curl virus - [Saudi Arabia] | TYLCV-[SA] |
| Tomato yellow leaf curl virus - [Shizuokua] AB014346 | YLCV-[Shi] |
| Tomato yellow leaf curl virus - [Spain7297] AF071228 | TYLCV-[ES7297] |
| Tomato yellow leaf curl virus - Iran AJ132711 | TYLCV-IR |
| Tomato yellow leaf curl virus - Mild X76319 | TYLCV-Mld |

Preferably the species of Begomovirus are TYLCCNV, TYLCGV, TYLCMaIV, TYLCSV, TYLCTHV, TYLCV, ACMV, BGMV, CaLCuV, ToCMoV, TGMV, ToGMoV, ToMHV, ToMoTV, ToMoV, ToRMV, ToSLCV, ToSRV, Cotton leaf curl (CLCrV, CLCuAV, ClCuGV, CLCuKV, CLCuMV, CLCuRV), East African cassava mosaic (EACMCV, EACMMV, EACMV, EACMZV), Potato yellow mosaic (PYMPV, PYMTV, PYMV), Squash leaf curl (SLCCNV, SLCV, SLCYV), Sweet potato leaf curl (SPLCGV, SPLCV), Tobacco leaf curl (TbLCJV, TbLCKoV, TbLCYNV, TbLCZV), Tomato leaf curl (ToLCBV, ToLCBDV, ToLCGV, ToLCKV, ToLCLV, ToLCMV, ToLCNDV, ToLCSLV, ToLCTWV, ToLCVV, ToLCV) and isolates thereof.

Other species of preferred geminivirus, belonging to the other genera Mastrevirus, Curtovirus, Topocuviruses, are WDV, MSV, SSV, BYDV, TYDV, BCTV and their isolates.

The gene sequence belonging to the genome of the geminiviruses can be the sequence C1/AL1/AC1, C2/AL2/AC2, C3/AL3/AC3, C4/AL4/AC4, V1/AR1/AV1, V2/AR2/AV2, BC1/BL1 and BV1/BR1, particularly, the sequence C1/AL1/AC1 of the previously described geminiviruses and their isolates.

The amino acid sequence encoded by the polynucleotide sequence object of the present invention is a pathogen-derived protein able to confer resistance against the geminiviruses to the plants expressing it. Said interfering protein since, according to the invention, is stably expressed, confers a lasting resistance independently from the molecular mechanism by which the protein product is able to induce resistance.

The pathogen-derived protein can be a capsid protein, replication-associated viral protein (Rep), proteins encoded by the genes C2/AL2/AC2, C3/AL3/AC3, C4/AL4/AC4, V2/AR2/AV2, BC1/BL1 and BV1/BR1.

An example of a possible polynucleotide sequence satisfying the above reported requirement is set forth in FIGS. 16A and 16B that show the alignment between the wild-type nucleotide sequence encoding the Rep-210 protein of the TYLCSV and the synthetic nucleotide sequence modified so as not to be a target of the post-trascriptional degradation induced by the infecting virus, where both nucleotide sequences encode the same viral protein.

The plants, tissues or plant cells that can be transformed with this polynucleotide sequences can be tomato, pepper, tobacco, sweet potato, cotton, melon, squash, manioc, potato, bean, soybean, mung bean, beet, sugar cane, corn, wheat.

It is a further object of the present invention a construct comprising an heterologous polynucleotide sequence containing in 5'-3' direction:

a) a polynucleotide sequence acting as promoter in said plant or tissue or transformed cells;

b) a non-translated polynucleotide sequence positioned at 5' of the encoding region, belonging or not to the intergenic region of geminivirus;

c) a polynucleotide sequence according to the invention or a fragment or a variant thereof;

d) a sequence acting as terminator of transcription, positioned at the 3' with respect to said polynucleotide sequence.

A further object of the present invention is an expression vector comprising the previously described construct.

Further it is an object of the present invention a plant, tissue or transgenic plant cells, progeny thereof as well as seeds comprising in their genome a polynucleotide sequence according to the present invention.

Finally, it is an object of the present invention a method for the preparation of transgenic plants, tissues or plant cells thereof long-lasting resistant to the geminiviruses that comprises the following steps:

a) "identification" or "selection" of a viral gene sequence encoding an amino acid sequence able to confer resistance against geminiviruses;

b) mutagenesis or "choice" of the viral gene sequence so as to make it an ineffective target of the post-trascriptional silencing induced by infecting geminivirus;

c) insertion of the geminivirus mutated or chosen gene sequence obtained in step b) through a construct as described previously, in the plant, tissue or plant cell thereof.

With reference to step a) of the method according to the present invention, the term "identification" means the experimental recognition of said viral gene sequence able to confer resistance against geminiviruses, while the term "selection" means the recognition of an already available viral gene sequence able to confer a not lasting resistance against geminiviruses. Accordingly, the method according to the present invention provides furthermore the solution to the problem of the loss of resistance against geminiviruses that occurs through the employment of known sequences.

Particularly, the mutagenesis predicted in step b) is carried out maintaining a nucleotide homology, with respect to the corresponding gene sequence of the geminiviruses against which it is required to obtain a resistance, lower or equal to 90%, preferably lower or equal to 80%, more preferably lower or equal to 70%, distributed so as the continuous homology in the transcribed RNA with respect to the corresponding sequence of geminiviruses is lower or equal to 17 nucleotides, preferably lower or equal to 8 nucleotides, more preferably lower or equal to 5 nucleotides and the maximum length of the sequence containing a single substitution with respect to the native gene sequence is not more than 30 nucleotides, preferably not more than 20 nucleotides, more preferably lower or equal to 9 nucleotides.

As the amino acid sequence encoded by the polynucleotide sequence identified or selected in step a), according to the present invention, it can be a protein having homology of 100% with respect to the viral wild-type protein.

This mutagenesis includes all those mutations on the nucleotide sequence that don't decrease the ability of the protein to confer resistance against geminivirus. Possible mutations are both silent point mutations and those leading to the substitution with amino acids having similar biochemical characteristics, or deletions and/or insertions and/or substitutions.

Alternatively, the mutagenesis in step b) of the method according to the present invention consists of deletions of the polynucleotide sequence at the extremities so as said sequence, while maintaining similar interfering abilities, is under-represented with respect to the original sequence, in the natural population of the siRNAs produced by the infecting virus.

Alternatively the "choice" in step b) of the method according to the present invention consists in the recognition of geminivirus wild-type sequences that differ at the nucleotidic level from the geminivirus against which it is required resistance so as not to be a target or to be an ineffective target of the post-trascriptional silencing.

Particularly, the mutagenesis action in step b) of the method according to the present invention can consist of deletions of the 3' or 5' region of the viral gene sequence of step a), until it is identified the minimum region of said gene sequence that is under-represented with respect to the sequence encoding a wild-type protein, in the population of the siRNAs and that said truncated protein maintains the ability to confer resistance against geminiviruses.

Moreover, the viral gene sequence of step a) of the method according to the present invention can be that of TYLCSV C1/AL1/AC1 gene and the amino acid sequence can be a protein truncated relatively to the viral wild-type protein such as, for instance, Rep-130.

Among various agronomic applications of the synthetic polynucleotide sequences according to the present invention, of particular interest is their use for obtaining tomato plants resistant to TYLCSV. In this particular embodiment, the transgenic polynucleotide sequence encoding the truncated viral Rep protein (Rep-210) has been modified through a 3'deletion resulting in an ineffective target of TYLCSV-induced post-trascriptional gene silencing, while maintaining the ability to confer resistance.

In particular, using stringent hybridizations with radioactive RNA probes, it was identified a transcribed region of the TYLCSV genome that is under-represented in the population of viral-origin siRNAs produced during the infection of the TYLCSV in wild-type plants, as shown in FIGS. 6 and 7. This region corresponds to the first 390 nucleotides of the gene encoding the TYLCSV Rep. Its transcript is an ineffective target of virus-induced post-trascriptional gene silencing, it encodes the Rep-130 protein which results stably expressed, resulting in a lasting resistance.

Therefore, in a particular embodiment of the invention, the amino acid sequence of geminiviruses, such as the TYLCSV, encoded by the polynucleotide sequence according to the invention can be the truncated Rep-130 protein (SEQ ID No 9). In this case the viral gene sequence made an ineffective or non target of the post-trascriptional silencing, is the SEQ ID No 8.

It's a further object of the present invention a method as described above wherein the mutagenesis in step b) consists of silent point mutations of the viral gene sequence of step a) that maintain the ability of the encoded amino acid sequence, to confer resistance against geminiviruses and to be an ineffective or non target of the post-trascriptional silencing.

Particularly, the viral gene sequence of step a) can be the V1/AR1/AV1 (CP) gene for instance of TYLCSV (SEQ ID No 12), and in a particular embodiment the viral gene sequence made ineffective or non target of the post-trascriptional silencing is the SEQ ID No 6.

In addition, the viral gene sequence of step a) can be the TYLCSV C1/AL1/AC1 gene, and in this case the viral gene sequence which was made ineffective or non target of the post-trascriptional silencing can be the SEQ ID No 2 or the SEQ ID No 4.

BRIEF DESCRIPTION OF THE DRAWINGS

The present invention now will be described by way of illustrating but not limiting way, according to preferred embodiments thereof, with particular reference to the figures of the enclosed drawings, wherein:

FIG. 1 shows the genome of tomato yellow leaf curl Sardinia specie virus (TYLCSV). DNA is transcribed bidirectionally and it contains six open reading frames partially or totally overlapping (ORF), two on the viral strand (V) V1 and V2 and four on the complementary strand (C) C1, C2, C3 and C4;

FIG. 2 shows the expression of Rep-210 protein in TYLCSV-agroinoculated transgenic *N. benthamiana* plants (line 102.22). The symbols (−), (+) and NI mean healthy, infected and non-inoculated plants, respectively. Analysis has been carried out before the agroinoculation with TYLCSV (0 wpi) and four and eight weeks after it (respectively 4 and 8 wpi);

FIG. 3 shows the expression of the Rep-210 protein and of the transgenic mRNAs in tomato plants (line 47×wt) before the agroinoculation with TYLCSV (0 wpi) and 22 weeks after it (22 wpi). The symbols (+) and (−) mean plants that are, respectively, infected or healthy at the specified time;

FIG. 4 shows the analysis of expression of Rep-210 protein and of the siRNAs corresponding to the relative transcript in transgenic tomato plants (47×10D line) before TYLCSV agroinoculation. The symbols (+) and (−) on the panel mean the presence and absence of the sense and antisense C1 transgene, respectively; wt means control wild-type plant; while the symbols (+), (−) and NI under the panel of the siRNAs mean the presence (+) and absence (−), respectively, of the virus and the non-agroinoculation (NI) as a control;

FIG. 5 shows the Northern blot of the small RNAs extracted from TYLCSV-infected wild-type tomato plants (samples 1-4) and non-infected as a control (sample C); M means a molecular weight marker;

FIG. 6 shows the distribution analysis of the small interfering RNAs with respect to the genome of the TYLCSV. On the top, the linear map of the TYLCSV genome; transcripts are pointed out by the arrows (V1 and V2 with the same polarity as the viral genome and C1, C2, C3 and C4 with complementary polarity); open boxes from 1 to 9 positioned under the viral genome map represent the nine PCR fragments (each about three hundred nucleotides in length), in which the genome has been divided and of which the ethidium bromide staining and hybridization with the siRNAs extracted by TYLCSV-infected tomato plants are shown. IR represents a tenth PCR fragment, corresponding to the non-transcribed intergenic region of the TYLCSV genome. The numbers under the panels mean the percentage of hybridization signal with respect to each PCR fragment;

FIG. 7 shows the analysis of the presence of siRNAs in non-agroinoculated (sample C) or TYLCSV-agroinoculated (samples 1 and 2) wild-type tomato plants at four weeks after inoculation; particularly the siRNAs corresponding to the transcript for Rep-210 (probe A) and for Rep-130 (probe B) were analyzed; the columns 100 and 50 on the left panels correspond to 100 and 50 pg, respectively, of an oligonucleotide homologous to both the A and B probes;

FIG. 8 shows the nucleotide sequence (SEQ ID No 8) encoding Rep-130 (SEQ ID No 9) of the pTOM130 plasmid. In capital, nucleotides not belonging to the TYLCSV but deriving from cloning; the underlined sequences correspond to BamHI and EcoRI restriction sites used for cloning. The start and stop codons are set forth in boldfaced while the mutations introduced for eliminating the C4 protein expression are in italic and boldfaced characters;

Figure 11:
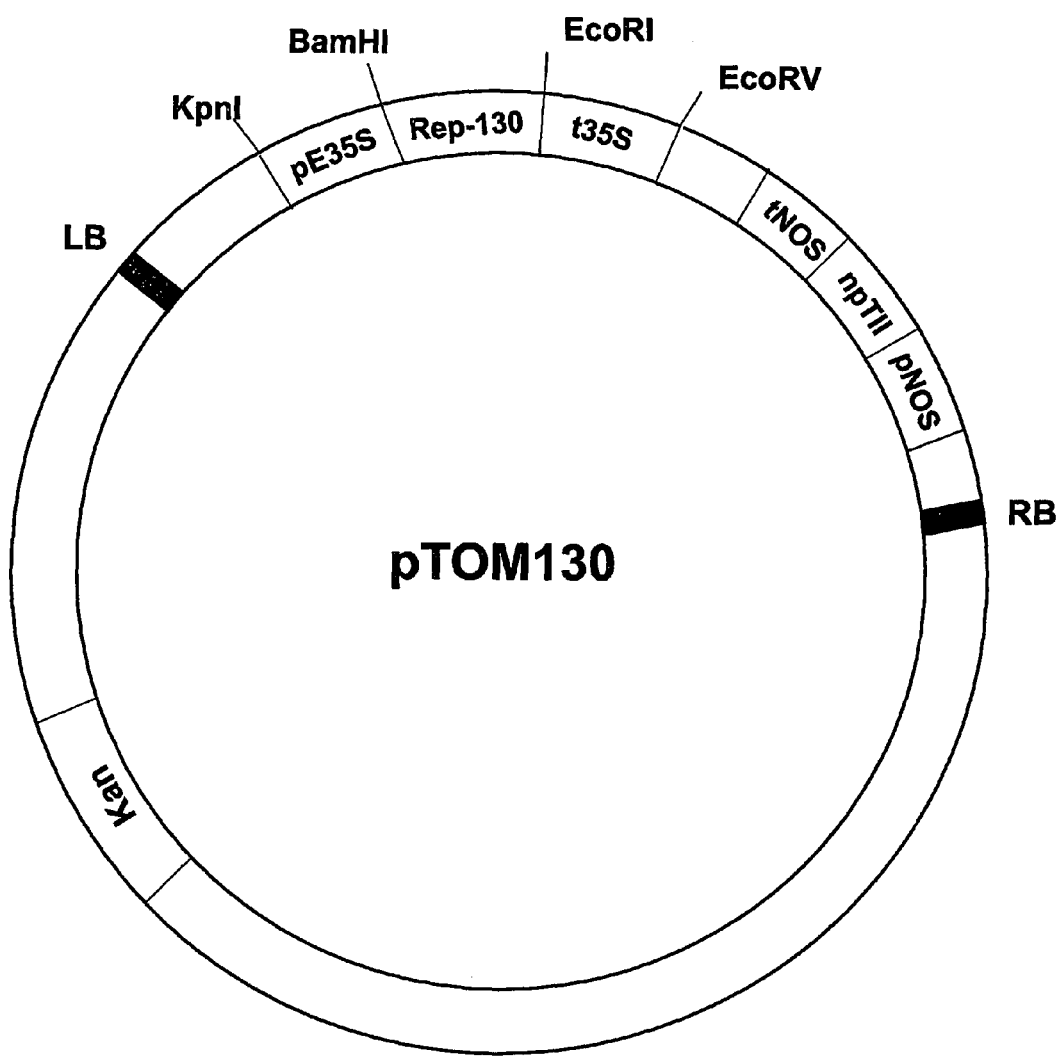
Figure 12:
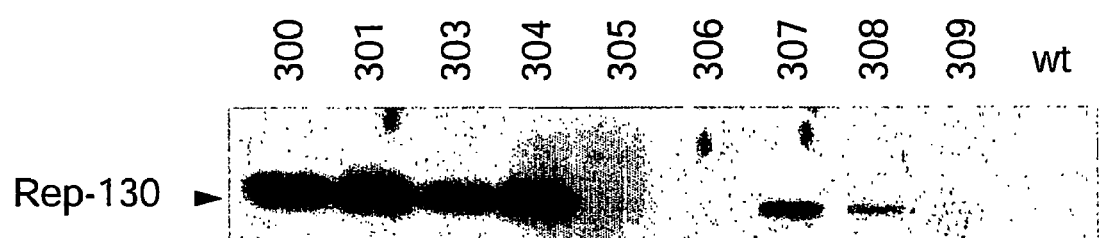
Figure 13:
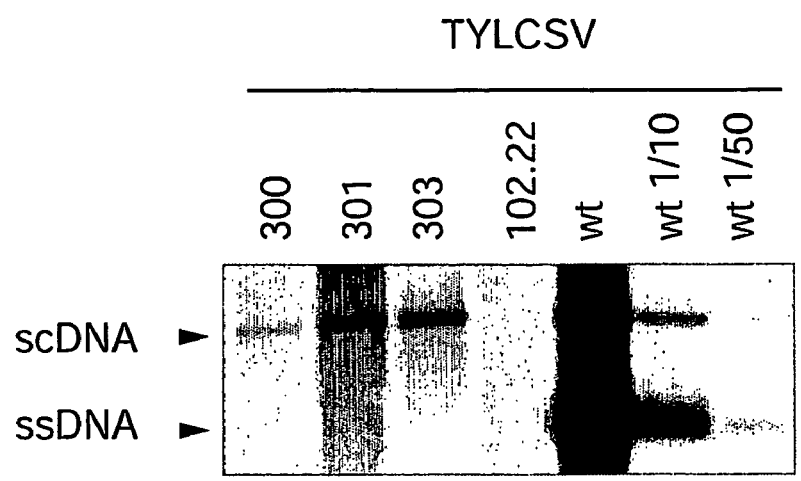

FIG. 11 shows the scheme of pTOM130 plasmid used for obtaining Rep-130-expressing transgenic plants. LB and RB mean left- and right-border respectively; pE35S represents the duplicated Cauliflower Mosaic Virus 35S promoter; Rep-130 (SEQ ID No 8) is the sequence encoding the Rep-130 protein (SEQ ID No 9); t35S is the Cauliflower Mosaic Virus 35S terminator; tNOS is the terminator of the gene encoding the nopalin synthase; nptII is the sequence encoding the neomycin phosphotransferase; pNOS is the promoter of the gene for the nopalin synthase; Kan is the gene for the kanamycin resistance;

FIG. 12 shows the analysis of the expression of Rep-130 protein (SEQ ID No 9) in transgenic *N. benthamiana* plants transformed with pTOM130 (lines 300-309);

FIG. 13 shows the analysis of the TYLCSV replication in wild-type (wt) and transgenic *N. benthamiana* protoplasts expressing either the Rep-130 protein (SEQ ID No 9) (lines 300, 301, 303) or the Rep-210 protein (102.22).

Figure 17:
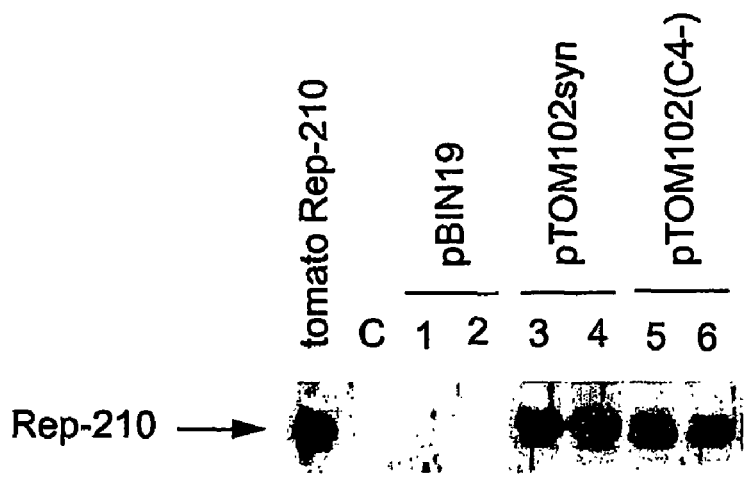
Figure 18:
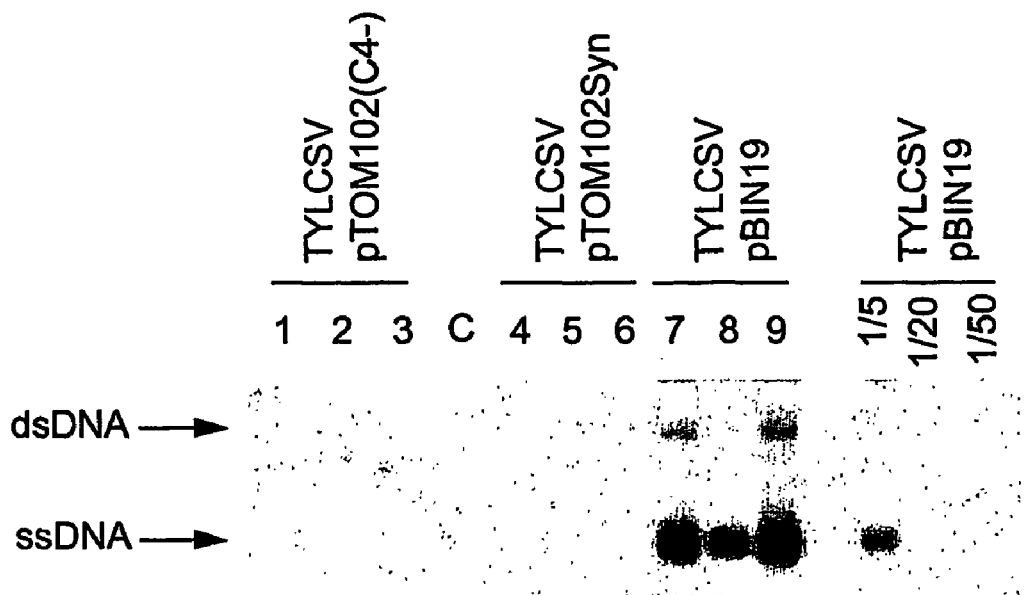
Figure 19:
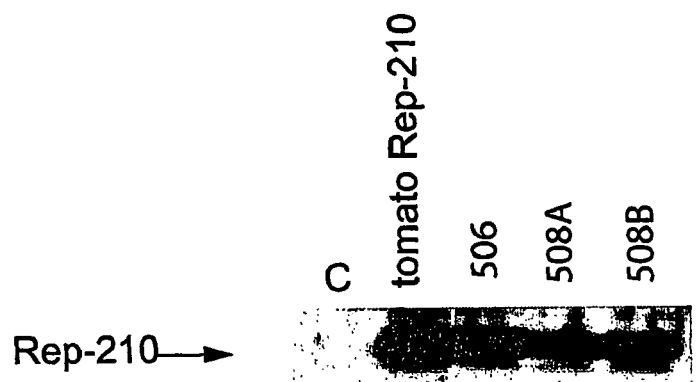
Figure 20:
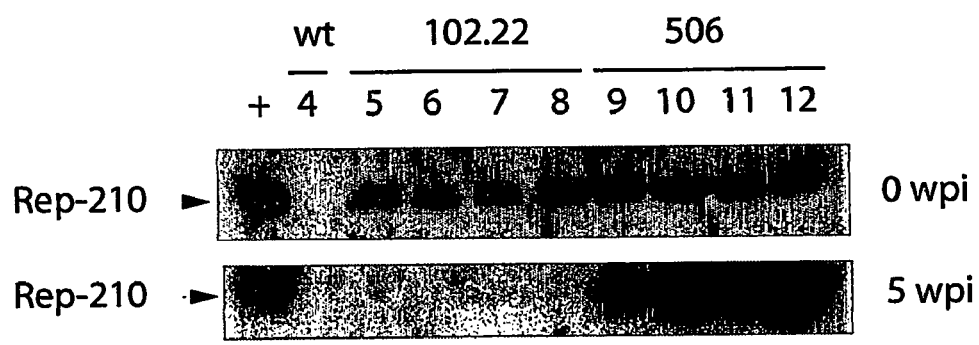
Figure 21:
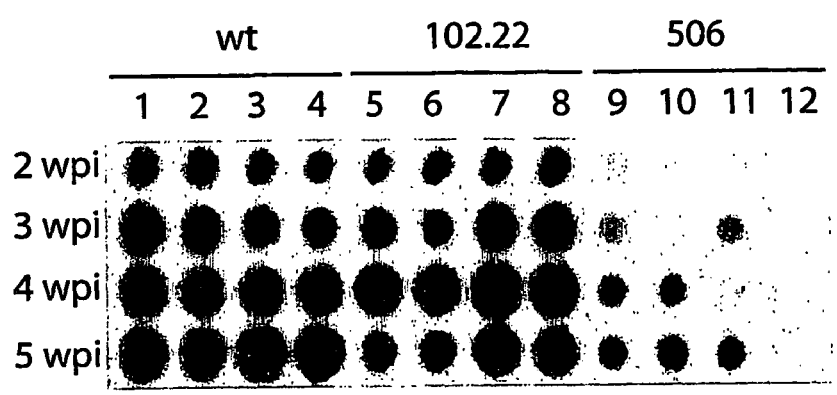

FIG. 14 shows the analysis of the expression of Rep-130 protein (SEQ ID No 9) in transgenic *L. esculentum* plants transformed with pTOM130 (lines 402, 403, 406, 411, 413, 416, 417). A protein extract from a transgenic Rep-130 expressing *N. benthamiana* (line 303) was used as positive control;

FIG. 15 shows the comparison between a *L. esculentum* transgenic plant transformed with pTOM130 (line 406) expressing Rep-130 and a non-transformed wild-type plant;

Figure 16A:
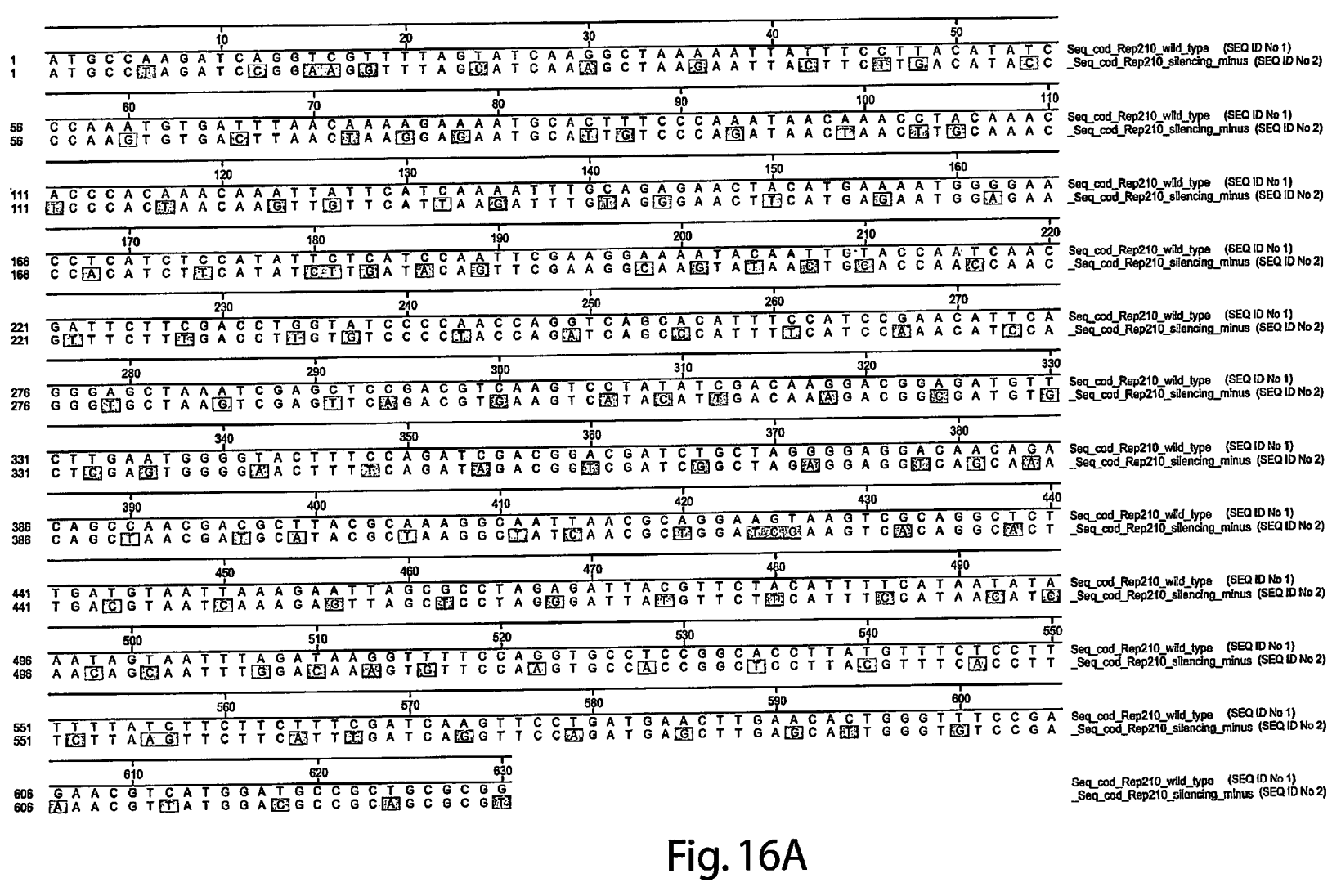

FIGS. 16 A and B shows two examples of synthetic sequences encoding Rep-210 (SEQ ID No 2, SEQ ID No 4). The alignment between the wild-type nucleotide sequence encoding TYLCSV Rep-210 protein (Seq_cod_Rep210_wild_type, on the top; SEQ ID No 1) and the synthetic nucleotide sequence modified so as to be an ineffective target of the virus-induced post-trascriptional silencing is shown (Seq_cod_Rep210_silencing_minus, in the bottom; SEQ ID No 2, SEQ ID No 4). In the synthetic sequences, the mutated nucleotides with respect to the wild-type sequence are shaded;

FIG. 17 shows the analysis of transient expression, by agroinfiltration into *N. benthamiana* leaves, of Rep-210 protein encoded by the plasmid wild-type gene pTOM102(C4−) and by the synthetic gene Rep-210 silencing minus B (SEQ ID No 4), (plasmid pTOM102 Syn);

FIG. 18 shows a transient assay for the inhibition of viral replication through co-agroinfiltration of an *A. tumefaciens* strain containing the TYLCSV infectious clone along with *A. tumefaciens* strains containing: a) the pTOM102(C4−) plasmid expressing the wild-type gene for Rep-210 SEQ ID No 1 (Brunetti et al., 2001), lines 1-3; b) the pTOM102Syn plasmid expressing the synthetic gene, for Rep-210 (Rep-210 silencing minus B; SEQ ID No 4) lines 4-6; c) the empty cloning plasmid pBIN19 lines 7-9;

FIG. 19 shows the analysis of the expression of Rep-210 protein in transgenic *N. benthamiana* plants transformed with pTOM102Syn plasmid containing the synthetic gene for Rep-210, Rep-210-silencing minus B, SEQ ID No 4 (lines 506, 508A and 508B). A protein extract from Rep-210-expressing transgenic tomato plant was used as positive control;

FIG. 20 shows the analysis of the expression of Rep-210 protein in transgenic *N. benthamiana* plants transformed with pTOM 102 (line 102.22, Noris et al., 1996) or with pTOM 102Syn (line 506) after TYLCSV agroinoculation. Analysis has been performed before (0 wpi) and five weeks after (5 wpi) TYLCSV agroinoculation;

FIG. 21 shows the analysis of the infection by "dot-blot" assay at 2, 3, 4, 5 wpi (where wpi means the number of weeks after the agroinoculation) on *N. benthamiana* wild-type (WT) or transgenic plants transformed with either pTOM 102 (line 102.22, Noris et al., 1996) or pTOM 102Syn (line 506);

Figure 22:
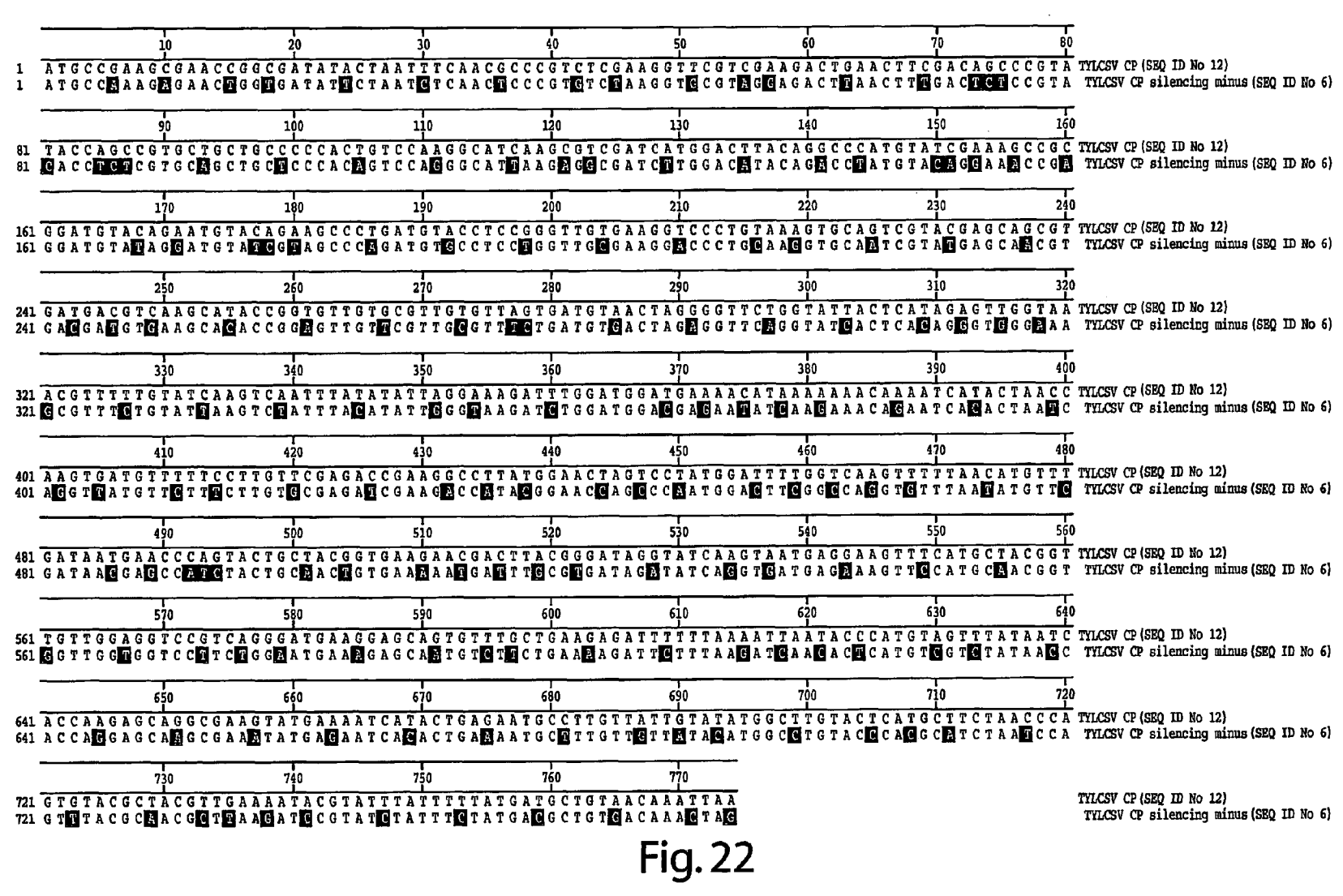

FIG. 22 shows an example of synthetic sequence encoding CP. The alignment between the wild-type nucleotide sequence encoding TYLCSV CP (TYLCSV CP, on the top; SEQ ID No 12) and the synthetic nucleotide sequence modified so as to be an extremely ineffective or non target of the virus-induced post-trascriptional degradation (TYLCSV CP silencing minus, in the bottom; SEQ ID No 6) is shown. In the synthetic sequence, the mutated nucleotides with respect to the wild-type sequence are shaded.

DETAILED DESCRIPTION OF THE INVENTION

Example 1

Figure 2:
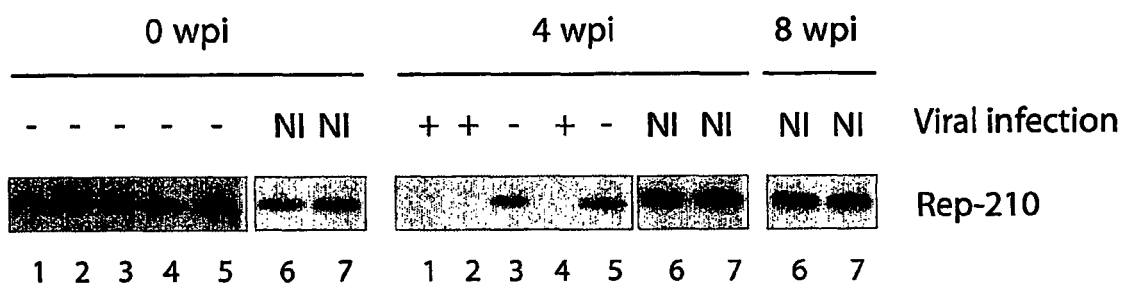
Figure 3:
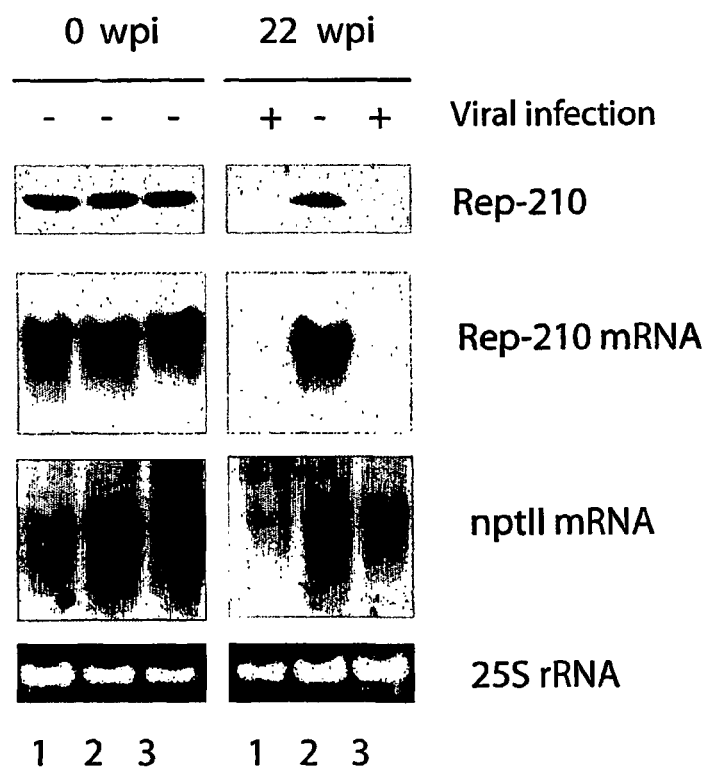
Figure 4:
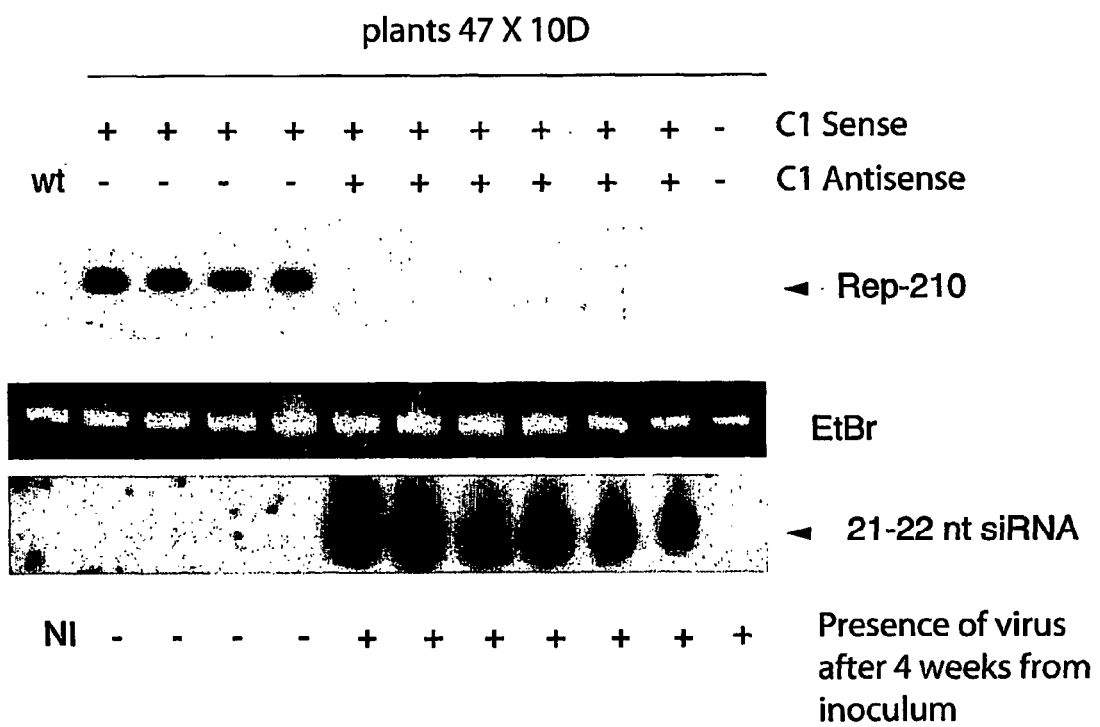
Figure 5:
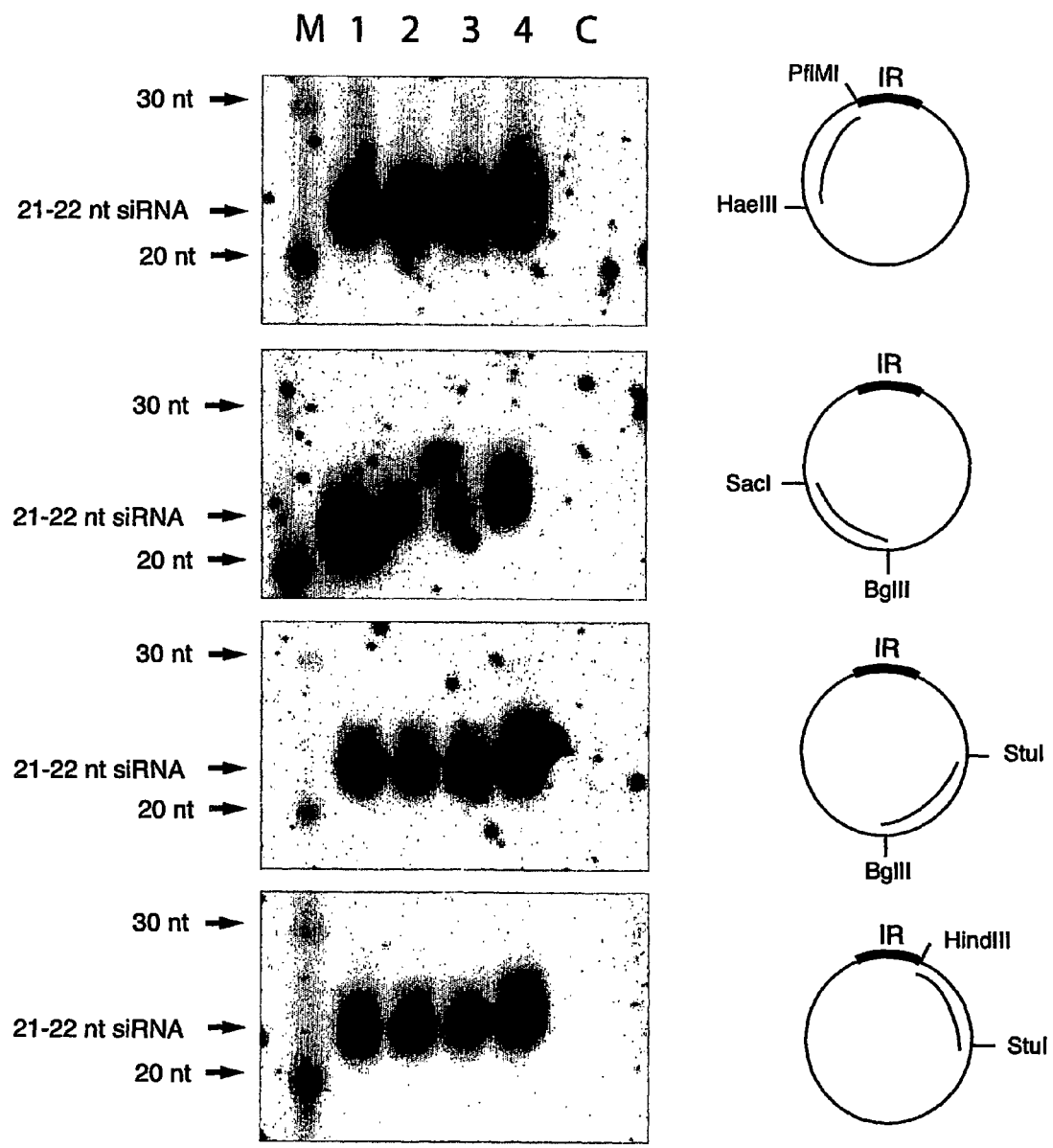

Identification of Regions of the TYLCSV Genome Under-Represented in the siRNAs Population In a natural infection by TYLCSV of wild-type plants, the viral sequences transcribed by both strands of TYLCSV genome are target of post-trascriptional gene silencing as pointed out by the presence of siRNAs homologous to different portions of the genome (FIG. 5). In FIG. 5 is shown the Northern blot of total RNAs extracted from the tomato wild-type plants infected by TYLCSV (samples 1-4) and non-infected control (sample C). Probe and the restriction sites used are indicated aside each panel. Also the estimated sizes of siRNAs are set forth.

Figure 6:
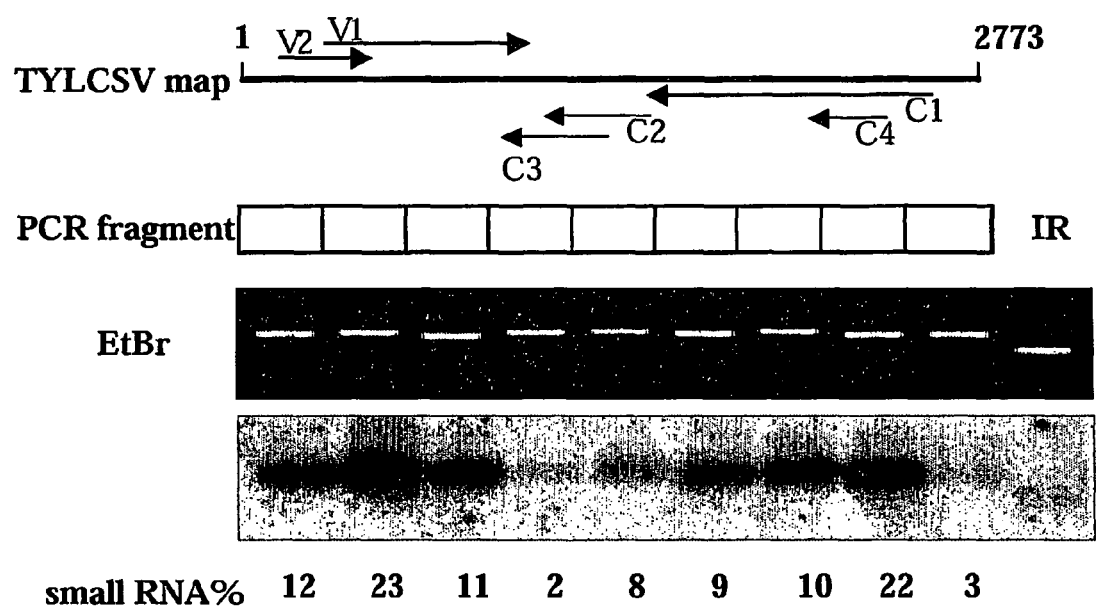

In order to evaluate if some regions of the TYLCSV genome constitute a target of post-trascriptional gene silencing less effective than others, it was performed a systematic study of the siRNA distribution with respect to their position on the viral genome. Therefore the TYLCSV genome has been divided in nine contiguous fragments, each of about three hundred base pairs (as drawn in FIG. 6), obtained by PCR with specific oligonucleotides. The same amount of such fragments has been transferred on nylon filter after agarose gel electrophoresis. Quantification of PCR fragments loaded on agarose gel has been performed by software Aida. The siRNAs produced by a TYLCSV-infected tomato plant have been purified starting from the total RNAs, terminally labelled and used as probe (Szittya et al., 2002) on the filter containing several regions of TYLCSV genome. The different intensity of the hybridization signals, referred to a same amount of loaded fragment, has been assessed through the TYPHOON apparatus (Amersham-Pharmacia). So a different distribution of the siRNAs with respect to the several regions of the viral genome has been detected (FIG. 6).

Example 2

Identification of a Region of TYLCSV C1 Gene Under-Represented in the si RNAs Population In order to identify a region of the TYLCSV C1 gene under-represented in the siRNAs population, total RNAs (Brunetti et al., 1997) both from healthy and TYLCSV-infected tomato plants have been extracted.

Thirty micrograms of such RNAs have been submitted to 8% denaturing polyacrylamide gel electrophoresis and transferred by capillarity on nylon filter through Northern blot. Two identical replicas have been produced and for each it has been carried out an hybridization with probes corresponding to different portions of the 5' region of the C1 gene, as shown in FIG. 7. One filter has been hybridized with a probe derived from the 5' portion of C1 gene comprising 42 nt of non-translated leader sequence and the first 630 nucleotides of C1 gene (about ⅗ of C1 gene) (probe A) and the other filter with a probe derived from the 5' portion of C1 gene comprising 42 nt of non-translated leader sequence and the first 390 nucleotides of C1 gene (probe B).

In order to quantitatively compare the results obtained by the two different probes (deriving from two independent labelling), scalar amounts of a same 40mer oligonucleotide complementary to both probes have been loaded on both replicas. Columns 100 and 50 correspond to 100 and 50 picograms of such oligonucleotide, respectively. The panels showing the oligonucleotide migration have been set close to the respective panels containing the siRNAs but their position in the figure doesn't correspond to the position on gel, because the oligonucleotide and the siRNAs have different molecular weights.

Both probes after in vitro transcription have been submitted to alkaline hydrolysis (Cox et al., 1984) in order to obtain from them fragments with an average length of 75 nucleotides.

The hybridizations have been performed for 16 hours at 39° C. in the buffer described by Dalmay et al., 2000. After hybridization the filters have been washed in 2×SSC, 0.2% SDS twice for 10 minutes at 40° C., twice for 10 minutes at 45° C. and once for 10 minutes at 50° C.

It is remarkable how the proximal 5' region of the C1 gene in the siRNAs population is under-represented. Particularly, the quantitative analysis of the results performed through the TYPHOON apparatus (Amersham-Pharmacia) revealed that the siRNAs corresponding to this 5' region are about 25% (probe B) with respect to those corresponding to the region extended up to nucleotides encoding the 210 amino acid (probe A). Said 5' region constitutes therefore an ineffective target for the virus-induced post-trascriptional gene silencing.

These results have been confirmed using the method described in example 1, i.e., where PCR fragments corresponding to the two different regions of the C1 gene were hybridised with the population of siRNA extracted from tomato plants infected by TYLCSV.

Example 3

Construction of a Polynucleotide Sequence of the C1 Gene 5' Portion Encoding the Truncated Rep As previously pointed out (Brunetti et al., 1997), the Rep-210 transgenic plants show a not long lasting resistance and an altered phenotype.

Figure 1:
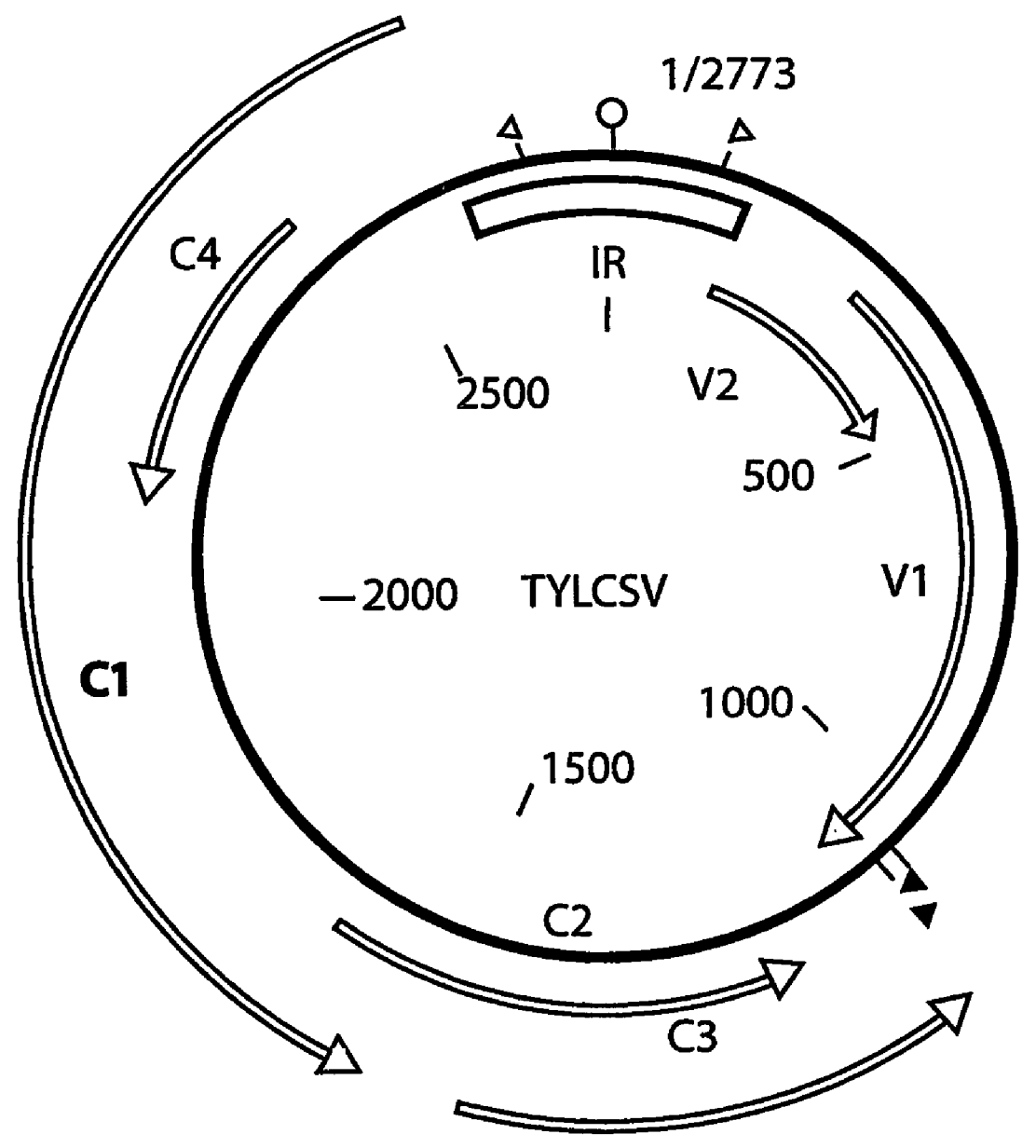

As can be noticed in FIG. 1, the C4 gene is nested in the truncated C1 gene in a different reading frame.

It is shown that the transgenic expression of geminivirus C4 gene induces phenotype alterations (Krake et al., 1998).

Therefore, it has been designed several truncated C1 constructs unable to express C4 ORF.

In order to obtain C4 (−) mutants, a stop codon has been introduced in the C4 sequence through the introduction of two point mutations. Particularly, referring to the pTOM130 sequence set forth in FIG. 8 (SEQ ID No 8), the mutation at nucleotide 233 consists of a trasversion from C to G that converts the TCA codon (encoding serine) of the reading frame encoding C4 in TGA (opal). In addition, the mutation at nucleotide 231 consists of a transition from C to T that restores in the reading frame encoding C1 a leucine codon (CTC becomes TTG, more represented in plant).

Thereby the translation of the C4 protein is interrupted after only 10 amino acids, while the amino acid sequence of the C1 protein remains unchanged. The two introduced mutations have been chosen among many possible mutations based on the criterion to generate a "strong" stop codon in the C4 reading frame, maintaining in the C1 reading frame a leucine codon compatible with codon usage in plants.

Mutagenesis has been performed by PCR with the following mutated oligonucleotides:

```
C4 plus.primer:
                                        (SEQ ID No 10)
5'-CT CAT CTC CAT ATT TTG ATC CAA TTC GAA G-3'

C4 minus.primer:
                                        (SEQ ID No 11)
5'-C TTC GAA TTG GAT CAA AAT ATG GAG ATG AG-3'
(2419-2448 in TYLCV-Kheyr-Pour et at., 1991)
```

Each of the two mutated primers has been used along with an external primer in two separate PCR reactions using pGEM102 as template (Brunetti et al., 2001).

Particularly, the external oligonucleotides are Rev and Univ (M13/pUC sequencing primer n.1233 and 1224). From the reaction performed with Univ/C4plus it has been obtained a 537 by fragment, while from the reaction with Rev/C4minus a 351 by fragment.

The obtained products have been used as templates for a following amplification reaction carried out using two external primers.

The obtained PCR product has been digested with EcoRI and BamHI restriction enzymes and cloned into the corresponding sites of pJIT60, thus obtaining pJITR210. In both cases it has been carried out the sequencing to verify clones.

Example 4

Identification of the Minimal 5' Region of TYLCSV C1 Gene that when Expressed in Plant Cells is Able to Inhibit Viral Replication In order to define the minimal 5' terminal region of C1 gene able to confer resistance against TYLCSV, a series of 3'-terminal deletion mutants of C1 gene was cloned in pJIT60 expression vector, resulting in a pJTR series.

The viral sequences have been amplified by PCR with Pfu DNA polymerase (Stratagene), using specific primers containing restriction sites at the ends.

The previously described pJITR210 plasmid, which encodes Rep-210, and contains a stop codon for the internal C4 protein, has been used as template. The fragments obtained by amplification reactions have been digested with BamHI and EcoRI enzymes and cloned in the corresponding sites of pJIT60 resulting in the pJTR series.

All final clones have been sequenced in order to confirm the amplification fidelity and vector-insert junctions. The length and the precise positions of every amplified sequence are set forth in table 6.

The ability of each Rep deletion mutant to confer resistance against TYLCSV has been evaluated through cotrasfection assays of N. benthamiana wild-type protoplasts with a TYLCSV infectious clone (pTOM6) along with each mutant, and following analysed for the replication level of the viral genome through Southern blot. The obtained results are set forth in FIGS. 9 and 10.

TABLE 6

| pJTR210a | 42 bp UTR + truncated C1 ORF (630 nt) containing C4 encoding region | 1985-2656 (1) |
|---|---|---|
| pJTR210 | 42 bp UTR + truncated C1 ORF (630 nt) | 1985-2656 (1) |
| pJTR181 | 42 bp UTR + truncated C1 ORF (543 nt) | 2072-2656 (1) |
| pJTR156 | 42 bp UTR + truncated C1 ORF (468 nt) | 2147-2656 (1) |
| pJTR130 | 42 bp UTR + truncated C1 ORF (390 nt) | 2225-2656 (1) |
| pJTR120 | 42 bp UTR + truncated C1 ORF (360 nt) | 2255-2656 (1) |
| pJTR80 | 42 bp UTR + truncated C1 ORF (240 nt) | 2375-2656 (1) |
| pJTR54 | 42 bp UTR + truncated C1 ORF (162 nt) | 2453-2656 (1) |

(1) nucleotide numbering of the TYLCSV genome are according to Kheyr-Pour et al. 1991.

The protoplast cotransfection, total nucleic acid extraction and Southern analysis have been performed according to already described methods (Brunetti et al. 2001).

Figure 9:
FIG. 9 shows the Southern blot of total nucleic acids extracts from wild-type *N. benthamiana* protoplasts cotransfected with a TYLCSV infectious clone (pTOM6), along with the plasmid expressing the mutated Rep protein indicated above each column.

Total nucleic acids extracts from each protoplast sample have been analysed through Southern blot with a digoxigenin-labelled RNA probe corresponding to the sequence encoding Rep-210, and the pGEM-P plasmid used as control. In particular FIG. 9 represents a Southern blot of total nucleic acids, where scDNA and ssDNA mean supercoiled and single strand DNA of TYLCSV, respectively.

For an accurate quantitative analysis of the effect of the expression of several truncated forms of Rep on the replication of TYLCSV genome, a Southern analysis has been performed with a $^{32}$P-labelled DNA probe corresponding to the region encoding the first 54 N-terminal amino acids of Rep and the radioactivity level corresponding to each band detected on filter has been evaluated, through analysis with the Istant Imager apparatus (Canberra, Packard).

Figure 10:
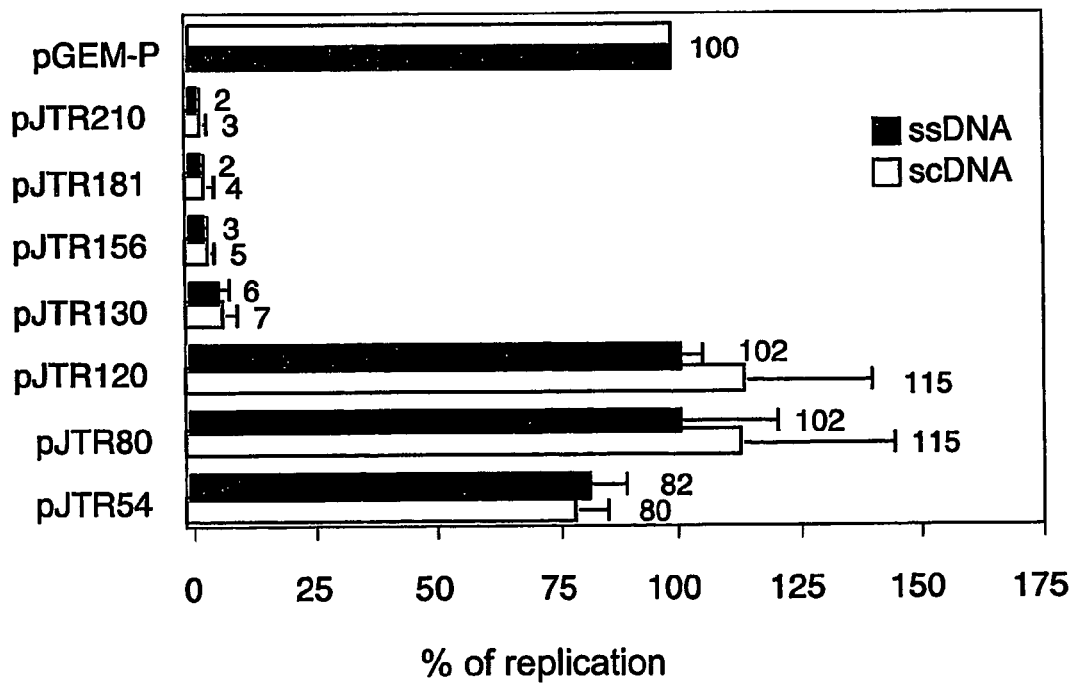
FIG. 10 shows the quantitative analysis of the TYLCSV replication in wild-type *N. benthamiana* protoplasts cotransfected with pTOM6 plasmid along with the plasmid expressing the mutated Rep protein.

Each mutated construct has been assayed in duplicate, in three independent experiments and the value set forth in FIG. 10 represents the average of two or three cotransfections of the three independent experiments.

The level of TYLCSV replication in the cotrasfection experiments performed with pTOM6 along with pGEM-P control plasmid was considered equal to 100%.

Particularly, FIG. 10 shows a quantitative analysis, the white and black bars of the histograms represents the amounts of supercoiled and single strand DNA, respectively; error bars indicates the mean standard deviation.

As pointed out by observing FIGS. 9 and 10, the first 130 N-terminal amino acids of the Rep protein are enough to inhibit almost completely viral replication, while the expression of the first 120 N-terminal amino acids has no influence.

Example 5

Production of N. Benthamiana Transgenic Plants Expressing Rep-130

The analysis of the ability to inhibit TYLCSV replication by the Rep mutants assessed through transient expression in protoplasts, has revealed that the shortest mutant still effective encodes Rep-130 (SEQ ID No 9) as described in the preceding example.

Also it has been previously revealed in other examples that the proximal 5' portion of C1 gene encoding Rep-130 is a less effective target of post-trascriptional gene silencing compared to sequence encoding Rep-210.

Therefore it has been obtained N. benthamiana transgenic plants expressing Rep-130. For this purpose, the pTOM130 plasmid represented in FIG. 11 has been obtained, by cloning KpnI-BglII fragment of pJTR130 into the KpnI-BamHI sites of pBIN19.

N. benthamiana has been transformed with the A. tumefaciens pGV2260 C58 strain containing pTOM130 plasmid and plants resistant to kanamycin have been regenerated as described (Noris et al. 1996).

The primary transformants have been analysed for the presence of transgene by PCR analysis and for the expression of Rep-130 protein through Western blot, as shown in FIG. 12.

The protein extracts obtained from transgenic (300-309) or wild-type control (wt) plants have been analysed by Western blot using an anti-TYLCSV Rep rabbit polyclonal primary antibody as described (Noris et al., 1996).

Example 6

Plant Cells Stably Transformed with the pTOM130 Construct and Expressing Rep-130 Inhibit TYLCSV Replication In order to early evaluate the resistance conferred by Rep-130, protoplasts isolated from several primary transgenic Rep-130 expressing N. benthamiana plants were transfected with a TYLCSV infectious clone (pTOM6).

Transgenic lines have been chosen for their high Rep-130 expression, as revealed by Western blot analysis (FIG. 12).

The level of TYLCSV replication in such transgenic protoplasts has been compared with that observed in N. benthamiana wild-type and in transgenic protoplasts expressing Rep-210 (line 102.22).

Particularly, FIG. 13 shows the analysis of TYLCSV replication in wild-type (wt) and transgenic N. benthamiana protoplasts expressing either Rep-130 (SEQ ID No 9) (lines 300, 301, 303), or Rep-210 (line 102.22). Total nucleic acids extracts from several protoplast samples have been analysed by Southern blot using a digoxigenin-labelled RNA probe corresponding to the Rep-210 transcript.

In order to compare the level of TYLCSV replication in the Rep-130 transgenic protoplasts with that observed in wild-type protoplasts, the total nucleic acids extracted from wild-type protoplasts have been also loaded following 1:10 and 1:50 dilutions, as shown in FIG. 13.

Example 7

Production of Tomato Transgenic Plants Expressing Rep-130

The analysis of the ability to inhibit TYLCSV replication by Rep mutants, assessed by transient expression in protoplasts, has revealed that the shortest mutant still effective encodes Rep-130, as described in the previous example.

As previously shown, the proximal 5' portion of C1 gene encoding Rep-130 is an ineffective target of post-trascriptional gene silencing compared with the sequence encoding Rep-210.

Therefore it has been carried out the production of transgenic tomato plants (*Lycopersicon esculentum* cv. Moneymaker) expressing Rep-130.

The tomato has been transformed using *A. tumefaciens* pGV2260 C58 strain containing pTOM130 plasmid (FIG. 11) and kanamycin-resistant plants were regenerated as described (Brunetti et al. 1997).

The primary trasformants have been analysed for the presence of the transgene by PCR analysis and for the expression of Rep-130 protein by Western blot (FIG. 14).

The protein extracts obtained from transgenic (lines 400) or wild-type control (wt) plants have been analysed by Western blot using an anti-TYLCSV Rep polyclonal rabbit primary antibody as described (Noris et al. 1996).

All transgenic tomato plants expressing Rep-130 protein are phenotypically impossible to distinguish from wild-type plants (FIG. 15).

Example 8

Demonstration of Long-Lasting Resistance Against TYLCSV in Plants Transgenic for the pTOM130 Construct Expressing Rep-130

In order to assess the lasting of the resistance against TYLCSV conferred by Rep-130 expression, the *N. benthamiana* R1 transgenic plants expressing Rep-130 have been agroinoculated with the *A. tumefaciens* LBA4404 strain containing the TYLCSV infectious clone.

As previously reported, the viral delivery through agroinoculation, used to assay the resistance and evaluate stability over time, corresponds to high or very high viral pressure conditions.

Infection of plants has been assessed at weekly intervals by a "tissue printing" assay, using a digoxigenin-labelled probe specific for the coat protein gene.

The results in table 7 show that, unlike the results described in table 2 concerning transgenic plants expressing Rep-210, transgenic *N. benthamiana* plants expressing Rep-130 protein show a long-lasting resistance when agroinoculated with TYLCSV. This can be deduced by comparison of the resistant plants at 2 and 6 weeks following inoculation.

TABLE 7

| Plants | Time (weeks) | N° infected plants/inoculated plants | % infected plants/ inoculated plants |
|---|---|---|---|
| Rep-130 | 2 | 0/10 | 0 |
| | 4 | 0/10 | 0 |
| | 6 | 0/10 | 0 |

TABLE 7-continued

| Plants | Time (weeks) | N° infected plants/inoculated plants | % infected plants/ inoculated plants |
|---|---|---|---|
| Wild-type | 2 | 9/10 | 90 |
| | 4 | 10/10 | 100 |

In addition, it was assessed the stability of the resistance against TYLCSV conferred by Rep-130 expression in transgenic R2 tomato plants.

The plants have been agroinoculated with the *A. tumefaciens* C58C1+pCH32 strain containing TYLCSV infectious clone. The agroinoculation conditions used for assaying the resistance and evaluating stability thereof over time, correspond to high or very high viral pressure conditions.

The infection has been assessed at intervals of one or two weeks through dot-blot assay, using a radioactively labelled probe specific for the coat protein gene.

The results in table 8 point out that tomato transgenic plants expressing Rep-130 show a long lasting resistance when agroinoculated with an TYLCSV infectious clone. This can be deduced from the comparison of the resistant plants at 3 and 12 weeks after inoculation.

TABLE 8

| Plants | Time (weeks) | N° infected plants/inoculated plants | % infected plants/ inoculated plants |
|---|---|---|---|
| Rep-130 | 3 | 0/9 | 0 |
| | 4 | 0/9 | 0 |
| | 5 | 0/9 | 0 |
| | 6 | 0/9 | 0 |
| | 7 | 0/9 | 0 |
| | 8 | 0/9 | 0 |
| | 10 | 0/9 | 0 |
| | 12 | 0/9 | 0 |
| segregating Rep-130 | 3 | 3/3 | 100 |
| Wild-type | 3 | 4/4 | 100 |

Therefore the resistance is associated to the presence of Rep-130 protein (SEQ ID No 9) and to the ability of TYLCSV-inoculated transgenic plant to stably express Rep-130, because the sequence encoding it is an ineffective target of virus-induced post-trascriptional gene silencing and Rep, even if further mutated, maintains its ability to confer virus resistance.

Example 9

Construction of a Synthetic Polynucleotide Sequence, Modified in Order not to be or to be an Extremely Ineffective Target of the Post-Trascriptional Gene Silencing Induced by the Infecting Virus, Encoding TYLCSV Rep-210 Protein In order to achieve the long lasting expression of TYLCSV Rep-210 protein in transgenic plants, it has been produced, employing the method according to the present invention, a synthetic polynucleotide sequence, able to encode for Rep-210 protein, that is not or is an ineffective target of the post-trascriptional gene silencing induced by the infecting virus.

In addition, the following criterions have been followed:

- the synthetic polynucleotide sequence is not able to encode the C4 protein, having in positions 231 and 233 the same mutations shown in FIG. 8, as described for Rep-130 (SEQ ID No 8; SEQ ID No 9).

the introduced mutations are all silent, namely the protein product encoded by the synthetic polynucleotide sequence matches that encoded by the viral wild-type sequence;

the mutations were introduced according to the frequency of codon usage in the tomato genes; particularly whenever possible the more frequently used codon in tomato was selected;

the introduced mutations have been all checked to exclude the possible formation of sequences having a particular function, such as for example polyadenilation or splicing signals, also cryptic.

Following the above described criterions, two synthetic sequences encoding Rep-210 have been designed (FIGS. 16 A and B, SEQ ID No 2, SEQ ID No 3, SEQ ID No 4, SEQ ID No 5).

A non-translated leader sequence at the 5' and a stop codon at the 3' have been added to the sequence of the synthetic Rep-210 silencing minus B gene (SEQ ID No 4).

Figure 16B:
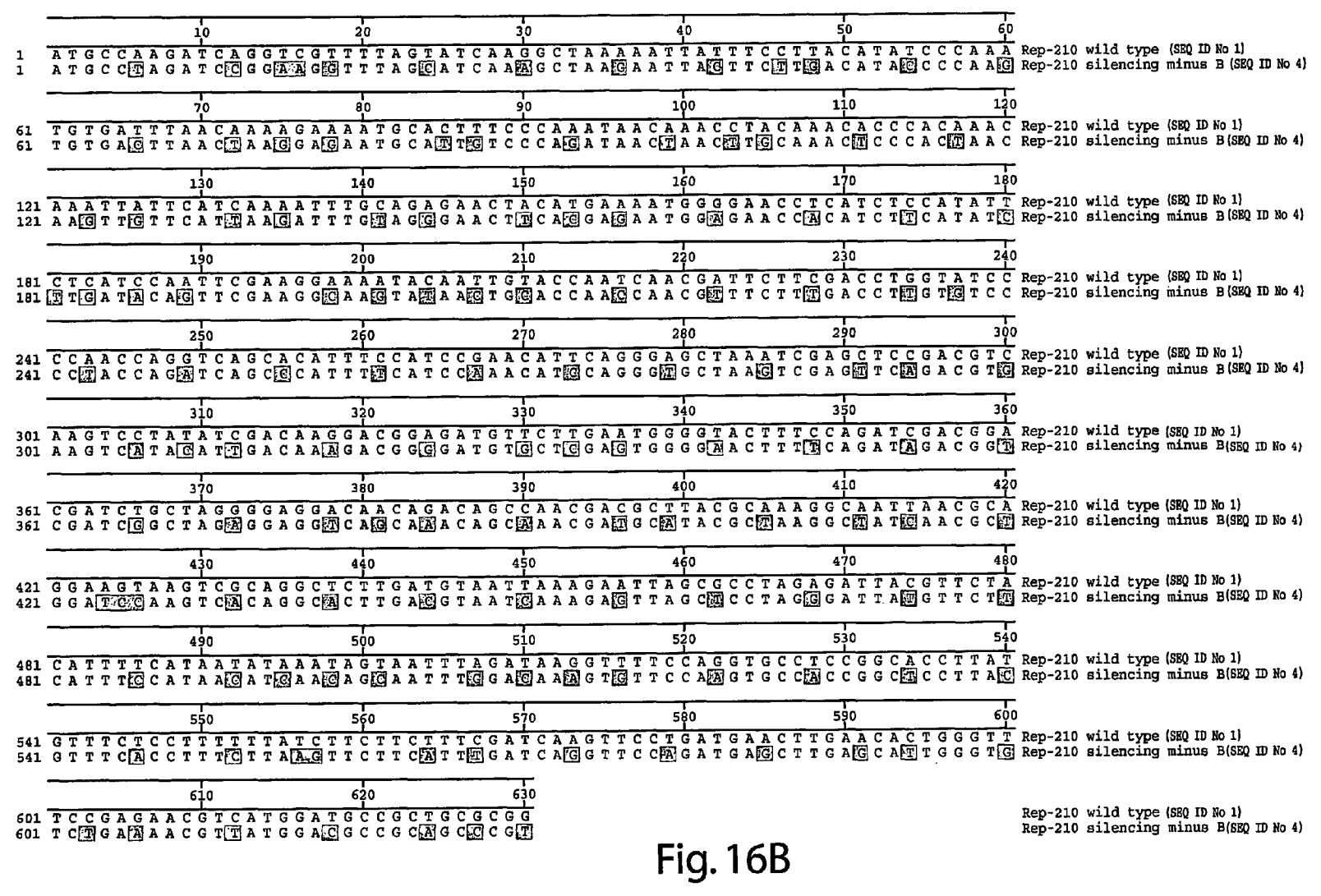

Particularly, the polynucleotide sequence containing in the 5'-3' order the non-translated leader sequence, the synthetic sequence encoding Rep-210 (FIG. 16B; SEQ ID No 4, SEQ ID No 5) and the stop codon has been assembled by PCR starting from oligonucleotides (Prodromou and Laurence, 1992; Stemmer et al., 1995), using a thermostable DNA polymerase with "proof reading" correction activity (Pfu DNA Polymerase, Stratagene and/or Pfx DNA Polymerase, Invitrogen).

The synthetic gene has been subsequently cloned in pJIT60 plasmid under the transcriptional control of 35S promoter of the Cauliflower mosaic virus (CaMV) and the transcription termination sequences of the CaMV 35S, producing the pJT60Syn. Then the cassette containing in the 5'-3' order: 35S promoter, Rep-210 synthetic gene, 35S terminator, has been removed from pJT60Syn plasmid by restriction with KpnI-BglII and cloned in the KpnI-BamHI sites of the binary plasmid pBIN19 generating pTOM102Syn.

Example 10

Evaluation of the Inhibition of Viral Replication by Rep-210 Synthetic Gene

The correct expression of Rep-210 protein, encoded by the synthetic gene, has been checked through agroinfiltration of N. benthamiana leaves, with A. tumefaciens C58C1/pCH32 transformed with pTOM102Syn. The strain C58C1/pCH32 transformed with pTOM102 (C4−) has been used as a positive control, while as negative control the strain C58C1/pCH32 transformed with the binary plasmid pBIN19 was used. Western blot analysis (FIG. 17) shows the expression of Rep-210 protein encoded by the synthetic gene.

In order to assess the ability of the Rep-210 protein, encoded by pTOM102Syn, to inhibit TYLCSV replication, a transient co-agroinfiltration assay has been carried out. N. benthamiana leaves have been co-agroinfiltrated with A. tumefaciens C58C1/pCH32 strain containing the TYLCSV infectious clone (pTOM6) along with the A. tumefaciens C58C1/pCH32 strain containing: a) pTOM102Syn plasmid; b) pTOM102 (C4−) plasmid; c) pBIN19 binary plasmid. The TYLCSV replication has been assessed through Southern analysis of the total nucleic acids extracted from the co-agroinfiltrated tissues 72 hours after the infiltration. This analysis has pointed out that Rep-210 protein expressed by the synthetic gene (pTOM102Syn) and by pTOM102(C4−) wild-type gene, inhibits TYLCSV replication in a similar manner (FIG. 18).

Example 11

Production of Transgenic N. Benthamiana Plants Expressing the Synthetic Gene for Rep-210

In order to obtain transgenic N. benthamiana plants expressing the synthetic gene for the Rep-210, N. benthamiana leaf-discs have been transformed using the A. tumefaciens LBA 4404 strain containing pTOM 102Syn plasmid and the kanamycin-resistant plants have been regenerated as described (Noris et al. 1996).

The primary trasformants have been analyzed for the expression of Rep-210 protein by Western blot analysis. Four primary trasformants, 506, 508, 517 and 537 lines accumulating intermediate levels of Rep-210 have been selected for further studies. FIG. 19 shows western analysis of proteins extracted from the 506, 508A and 508B plants.

Example 12

Stability of the Resistance in N. Benthamiana Transgenic Plants for Rep-210 Synthetic Gene The authors have previously shown (Noris et al. 1996; Brunetti et al. 1997) that there is a direct correlation between the amounts of Rep-210 protein produced by the transgenic plants and resistance against TYLCSV. Transgenic plants transformed with the pTOM102 construct accumulating intermediate levels of Rep-210 protein are susceptible to viral infection, like non-transformed plants (Noris et al. 1996 and unpublished data). The low level of Rep-210 protein in these plants is not enough to completely inhibit viral replication, thus allowing the establishment of an early virus-induced post-trascriptional silencing leading to a drastic reduction in Rep-210 protein accumulation which causes lack of resistance.

In order to assess if Rep-210 protein encoded by the synthetic gene is not or is an ineffective target of virus-induced post-trascriptional gene silencing and therefore to control over time the viral infection, line 102.22 transgenic plants (R3) and line 506 transgenic plants (R0) expressing similar amount of Rep-210 (FIG. 20, 0 wpi), have been agro-inoculated with the TYLCSV and analysed by dot blot at week intervals for the accumulation of the TYLCSV. As expected (Noris et al., 1996) the transgenic R3 line 102.22 plants (FIG. 21, 5-8) that accumulate intermediate levels of Rep-210 protein are susceptible as the non-transformed plants (FIG. 21, 1-4). As shown by dot blot analysis (FIG. 21, 9-12) the transgenic plants for the synthetic construct (R0 line 506) are resistant to viral infection, accumulating only limited amounts of virus. Interestingly and according to virus inability to post-transcriptionally silence effectively the synthetic gene, Rep-210 was still accumulating 5 weeks after inoculum (FIG. 20, 5 wpi) and inhibiting over time TYLCSV replication (FIG. 21, 9-12).

The results described in the examples point out that it is possible to obtain a long lasting resistance against geminiviruses by expressing in plant a transgene consisting of a pathogen-derived polynucleotide sequence, if the latter is suitably selected or modified in order not to be a target or to be an ineffective target of the post-trascriptional gene silencing by the infecting virus.

Example 13
Construction of a Synthetic Polynucleotide Sequence Modified in Order not to be a Target or to be an Extremely Ineffective Target, of the Post-Trascriptional Degradation Induced by the Infecting Virus, Encoding the TYLCSV Capsid Protein As above reported, the transgenic expression of the TYLCV capsid protein in a interspecific tomato hybrid (*Lycopersicon esculentum* X *L. pennellii*) confers a partial resistance against viral infection (Kunik et al., 1994). Also in this case, the resistance mediated by the expression of the capsid protein is not long lasting.

In order to obtain a stable expression of the TYLCSV capsid protein (CP) by transgenic plants, it has been produced a synthetic polynucleotide sequence, able to encode the CP, which results in an ineffective target of virus-induced post-trascriptional gene silencing.

The synthetic polynucleotide sequence has been designed so as to satisfy the requisite not to be or to be an extremely ineffective target of virus-induced post-trascriptional gene silencing employing the method according to the present invention.

In addition, the following criterions have been followed:
- the introduced mutations are all silent, namely the protein product encoded by the synthetic polynucleotide sequence is exactly matching that encoded by the viral wild-type sequence;
- the introduced mutations consider the frequency of codon usage in the tomato genes; particularly whenever possible the codon more frequently used in tomato is selected;
- the introduced mutations have been all checked to exclude the possible formation of sequences having a particular function, such as for example polyadenilation signals or splicing signals, also cryptic.

Following the above described criterions a synthetic sequence encoding CP has been designed (SEQ ID No 12) (FIG. 22, TYLCSV CP silencing minus, SEQ ID No 6, SEQ ID No7).

BIBLIOGRAPHY

Abel P P, Nelson R S, De B, Hoffmann N, Rogers S G, Fraley R T, Beachy R N. 1986. Delay of disease development in transgenic plants that express the tobacco mosaic virus coat protein gene. Science 232:738-43.

Baulcombe D C 1996. Mechanisms of Pathogen-Derived Resistance to Viruses in Transgenic Plants. 8:1833-1844.

Beachy, R. 1997. Mechanisms and applications of pathogen-derived resistance in transgenic plants. Current Opinion in Biotechnology 8:215-220.

Briddon, R. W. and P. G. Markham. 1995. Geminiviridae, Sixth report of international committee on taxonomy of viruses. Springer-Verlag, New York, N.Y.

Brunetti, A., R. Tavazza, E. Noris, A. Lucioli, G. P. Accotto, and M. Tavazza, 2001, J. Virol. 75:10573-81.

Cahill, M., K. Gorman, S. Kay and I. Denliolm. 1996. Baseline determination and detection of resistance to imidacloprid in *Bemisia tabaci* (Homoptera: Aleyrodidae) Bulletin of Entomology. Research 86:343-349.

Cox, K. H., D. V. DeLeon, L. M. Angerer, and R. C. Angerer. 1984. Detection of mrnas in sea urchin embryos by in situ hybridization using asymmetric RNA probes. Dev Biol 101:485-502

Czosnek, H., and H. Laterrot. 1997. A world survey of tomato yellow leaf curl viruses. Archives of Virology 142:1391-1406.

Dalmay, T., A. Hamilton, E. Mueller, and D. C. Baulcombe. 2000. Potato virus X amplicons in arabidopsis mediate genetic and epigenetic gene silencing. Plant Cell 12:369-379.

English J., Mueller E., and Baulcombe D. C. 1996. Suppression of Virus Accumulation in Transgenic Plants Exhibiting Silencing of Nuclear Genes. Plant Cell. 8: 179-188.

Fauquet C M, Bisaro D M, Briddon R W, Brown J K, Harrison B D, Rybicki E P, Stenger D C, Stanley J. 2003. Revision of taxonomic criteria for species demarcation in the family Geminiviridae, and an updated list of begomovirus species. Arch Virol. 148:405-21.

Hanley-Bowdoin, L., S. B. Settagle, B. M. Orozco, S. Nagar and D. Robertson. 1999. Geminivirus: models for plant DNA replication, transcription, and cell cycle regulation. Critical Reviews in Plant Sciences, 18:71-106.

Kheyr-Pour A., M. Bendahmane, V. Matzeit, G. P. Accotto, S. Crespi and B. Gronenborn. 1991. Tomato yellow leaf curl virus from Sardinia is a whitefly-transmitted monopartite Geminivirus. Nucleic Acids Research 19:6763-6769. Picò, B., M. J. Diez and F. Nuez. 1996. Viral disease causing economic losses to the tomato crop. II. The tomato yellow leaf curl virus review. Scientia Horticulturae 67:151-196.

Krake, L. R., M. A Rezaian, and I. B. Dry. 1998. Expression of the tomato leaf curl Geminivirus C4 gene produces viruslike symptoms in transgenic plants Molecur Plant Microbe Interactions 11:413-417.

Kunik, T., R. Salomon, D. Zamir, N. Navot, M. Zeidan, I. Michelson, Y. Gafni and H. Czosnek 1994. Transgenic tomato plants expressing the tomato yellow leaf curl virus capsid protein are resistant to the virus. Bio/technology 12:500-504.

Noris, E., G. P. Accotto, R. Tavazza, A. Brunetti, S. Crespi, and M. Tavazza. 1996. Resistance to tomato yellow leaf curl Geminivirus in *Nicotiana benthamiana* plants transformed with a truncated viral C1 gene [published erratum appears in Virology 1997 Jan. 20; 227(2):519]. Virology 224:130-8.

Polston, J. E. and P. K. Anderson. 1997. The emergence of whitefly-transmitted gemini viruses in tomato in the Western hemisphere. Plant Disease 81:1358-1369.

Prodromou, C. and L. H. Pearl. 1992. Recursive PCR: a novel technique for total gene synthesis: Protein Engineering, 5:827-829.

Sangaré, A., D. Deng, C. M. Fauquet and R. Beachy. 1999. Resistance to African cassava mosaic virus conferred by a mutant of the putative NTP-binding domain of the Rep gene (AC1) in *Nicotiana benthamiana*. Molecular Biology Reports 5:95-102.

Stemmer, W. P. C., A. Crameri, K. D. Ha, T. M. Brennan, H. L. Heyneker. 1995. Single-step assembly of a gene and entire plasmid from large numbers of oligodeoxyribonucleotides. Gene, 164:49-53.

Szittya, G., D. Silhavy, A. Molnar, C. Hornyik, J. Burgyan. 2002. Short Defective Interfering RNAs of Tombusviruses Are Not Targeted but Trigger Post-Transcriptional Gene Silencing against Their Helper Virus. The Plant cell, Vol. 14, 359-372.

Szittya, G., D. Silhavy, A. Molnar, Z. Havelda, A. Lovas, L. Lakatos, Z. Banfalvi and J. Burgyan. 2003. Low temperature inhibits RNA silencing-mediated defence by the control of siRNA generation. EMBO Journal 22:1-8.

Tavazza, M., A. Lucioli. 1993. Approcci Molecolari per la Resistenza alle Virosi. In "Miglioramento Genetico per Resistenza a Patogeni e Parassiti." Fondamenti Teorici e Pratici. Buiatti M., Crinò P., Porta-Puglia F., Saccardo F., Sonnino A., Surico G. (Editori). Ed. Agricole Bologna. 191-214.

Voinnet, O. 2001. RNA silencing as a plant immune system against viruses. Trends in Genetics 17:449-459.

Waterhouse, P. M., M. B. Wang and T. Lough. 2001. Gene silencing as an adaptive defence against viruses. Nature 411:834-842.

Williams, L., T. J. Dennehy and J. C. Palumbo 1996. Development of a resistance management program for imidacloprid "Proc. Beltwide Cotton Conferences pp. 752-755.

Zaitlin M. and Palukaitis P. 2000. Advances in understanding plant viruses and virus diseases. Annual review of phytopathology 38: 117-143.

The invention claimed is:

1. A mutated C1/AL1/AC1 polynucleotide sequence of a tomato infecting geminivirus, wherein the mutations consist of silent point mutations distributed along the C1/AL1/AC1 polynucleotide sequence in such a way that continuous homology between the mutated C1/AL1/AC1 polynucleotide sequence and the wild-type C1/AL1/AC1 polynucleotide sequence is less than or equal to 8 nucleotides, said mutated C1/AL1/AC1 polynucleotide sequence encoding for a truncated Rep protein.

2. The mutated C1/AL1/AC1 polynucleotide sequence according to claim 1, wherein the continuous homology between the mutated C1/AL1/AC1 polynucleotide sequence and the wild-type C1/AL1/AC1 polynucleotide sequence is less than or equal to 5 nucleotides.

3. The mutated C1/AL1/AC1 polynucleotide sequence according to claim 1, encoding truncated Rep proteins consisting of 130 amino acids (Rep-130) to 210 amino acids (Rep-210), said truncation occurring at the 3' terminal.

4. The mutated C1/AL1/AC1 polynucleotide sequence according to claim 3, having the sequence of SEQ ID NO: 4, said polynucleotide sequence encoding for Rep-210 protein having the amino acid sequence of SEQ ID No 5 NO: 5.

5. The mutated gene C1/AL1/AC1 polynucleotide sequence according to claim 1 wherein the tomato infecting geminivirus is Tomato yellow leaf curl Sardinia virus (TYLCSV).

6. A construct comprising an heterologous polynucleotide sequence containing in the 5'-3' direction:
   a) a polynucleotide sequence acting as promoter in plant, plant tissue or plant cells;
   b) a non-translated polynucleotide sequence positioned 5' of the encoding region of the mutated geminivirus C1/AL1/AC1 polynucleotide sequence;
   c) a mutated C1/AL1/AC1 polynucleotide sequence as defined according to claim 1; and
   d) a polynucleotide sequence acting as transcription terminator, positioned 3' with respect to the mutated C1/AL1/AC1 polynucleotide sequence.

7. An expression vector comprising the construct as defined according to claim 6.

8. A transgenic plant, or plant tissue or plant cells thereof, comprising a mutated C1/AL1/AC1 polynucleotide sequence as defined according to claim 1.

9. Seed A seed comprising a mutated C1/AL1/AC1 polynucleotide sequence as defined according to claim 1.

10. A method for the preparation of transgenic plants, plant tissue or cells thereof having long lasting resistance against geminiviruses, including the following steps:
   a) selection of a geminivirus C1/AL1/AC1 polynucleotide sequence encoding an amino acid sequence conferring resistance against geminiviruses, said resistance being overcome over time by geminivirus induced post-transcriptional transgene silencing;
   b) mutagenesis of the selected geminivirus C1/AL1/AC1 polynucleotide sequence, wherein the mutations consist of silent point mutations distributed along the geminivirus C1/AL1/AC1 polynucleotide sequence so that continuous homology between the mutated C1/AL1/AC1 polynucleotide sequence and the selected C1/AL1/AC1 polynucleotide sequence is less than or equal to 8 nucleotides; and
   c) insertion of the geminivirus C1/AL1/AC1 polynucleotide sequence mutated in the step b) in the plant, plant tissue or cell thereof, using a construct comprising an heterologous polynucleotide sequence containing in the 5'-3' direction:
      i) a polynucleotide sequence acting as a promoter in said plant, plant tissue or cells;
      ii) a non-translated polynucleotide sequence positioned 5' of the encoding region of the mutated geminivirus C1/AL1/AC1 polynucleotide sequence;
      iii) a mutated C1/AL1/AC1 polynucleotide sequence mutagenized according to step (b) encoding a geminivirus amino acid sequence, wherein the mutated C1/AL1/

AC1 polynucleotide sequence is an ineffective target of the geminivirus induced post-transcriptional transgene silencing; and iv) a polynucleotide sequence acting as a transcription terminator positioned 3' with respect to said mutated C1/AL1/AC1 polynucleotide sequence.

11. The method according to claim 10, wherein the geminiviruses are selected from the species belonging to the Begomovirus genus and isolates thereof.

12. The method according to claim 11, wherein the Begomoviruses species is Tomato yellow leaf curl Sardinia virus (TYLCSV).

13. The method according to claim 12, wherein the selected geminivirus C1/AL1/AC1 polynucleotide sequence encodes a truncated protein with respect to the geminivirus wild-type protein.

14. The method according to claim 13 wherein the mutated geminivirus C1/AL1/AC1 polynucleotide sequence made an ineffective target of the geminivirus-induced post-transcriptional transgene silencing is SEQ ID NO: 4.

15. The method according to claim 14, wherein the truncated protein is Rep-210 having the sequence of SEQ ID NO: 5.

16. The method according to claim 10, wherein the plants, plant tissues or cells thereof belong to a member selected from the group consisting of tomato, pepper, tobacco, squash, manioc, sweet potato, cotton, melon, potato, soybean, corn, wheat, sugar cane, bean, and beet.

17. The method according to claim 10, wherein the continuous homology between the mutated C1/AL1/AC1 polynucleotide sequence and the selected C1/AL1/AC1 polynucleotide sequence is less than or equal to 5 nucleotides.

* * * * *

SEQUENCE LISTING

<160> NUMBER OF SEQ ID NOS: 12

<210> SEQ ID NO 1
<211> LENGTH: 630
<212> TYPE: DNA
<213> ORGANISM: Geminivirus TYLCSV

<400> SEQUENCE: 1

```
atgccaagat caggtcgttt tagtatcaag gctaaaaatt atttccttac atatcccaaa      60
tgtgatttaa caaagaaaaa tgcactttcc caaataacaa acctacaaac acccacaaac     120
aaattattca tcaaaatttg cagagaacta catgaaaatg gggaacctca tctccatatt     180
ctcatccaat tcgaaggaaa atacaattgt accaatcaac gattcttcga cctggtatcc     240
ccaaccaggt cagcacattt ccatccgaac attcagggag ctaaatcgag ctccgacgtc     300
aagtcctata tcgacaagga cggagatgtt cttgaatggg gtactttcca gatcgacgga     360
cgatctgcta ggggaggaca acagacagcc aacgacgctt acgcaaaggc aattaacgca     420
ggaagtaagt cgcaggctct tgatgtaatt aaagaattag cgcctagaga ttacgttcta     480
cattttcata atataaatag taatttagat aaggttttcc aggtgcctcc ggcacccttat    540 gtttctcctt ttttatcttc ttctttcgat caagttcctg atgaacttga acactgggtt     600
tccgagaacg tcatggatgc cgctgcgcgg                                      630
```

<210> SEQ ID NO 2
<211> LENGTH: 630
<212> TYPE: DNA
<213> ORGANISM: Artificial
<220> FEATURE:
<223> OTHER INFORMATION: TYLCSV Rep-210 modified sequence
<220> FEATURE:
<221> NAME/KEY: CDS
<222> LOCATION: (1)..(630)

<400> SEQUENCE: 2

```
atg cct aga tcc gga agg ttt agc atc aaa gct aag aat tac ttc ttg        48
Met Pro Arg Ser Gly Arg Phe Ser Ile Lys Ala Lys Asn Tyr Phe Leu
1               5                   10                  15 aca tac ccc aag tgt gac tta act aag gag aat gca ttg tcc cag ata        96
Thr Tyr Pro Lys Cys Asp Leu Thr Lys Glu Asn Ala Leu Ser Gln Ile
                20                  25                  30 act aac ttg caa act ccc act aac aag ttg ttc att aag att tgt agg       144
Thr Asn Leu Gln Thr Pro Thr Asn Lys Leu Phe Ile Lys Ile Cys Arg
            35                  40                  45 gaa ctt cat gag aat gga gaa cca cat ctt cat atc ttg ata cag ttc       192
Glu Leu His Glu Asn Gly Glu Pro His Leu His Ile Leu Ile Gln Phe
        50                  55                  60 gaa ggc aag tat aac tgc acc aac caa cgt ttc ttt gac ctt gtg tcc       240
Glu Gly Lys Tyr Asn Cys Thr Asn Gln Arg Phe Phe Asp Leu Val Ser
65                  70                  75                  80 cct acc aga tca gcc cat ttt cat cca aac atc cag ggt gct aag tcg       288
Pro Thr Arg Ser Ala His Phe His Pro Asn Ile Gln Gly Ala Lys Ser
                85                  90                  95 agt tca gac gtg aag tca tac att gac aaa gac ggc gat gtg ctc gag       336
Ser Ser Asp Val Lys Ser Tyr Ile Asp Lys Asp Gly Asp Val Leu Glu
                100                 105                 110
```

-continued

```
tgg gga act ttt cag ata gac ggt cga tcg gct aga gga ggt cag caa         384
Trp Gly Thr Phe Gln Ile Asp Gly Arg Ser Ala Arg Gly Gly Gln Gln
    115                 120                 125 aca gct aac gat gca tac gct aag gct atc aac gct gga tcc aag tca         432
Thr Ala Asn Asp Ala Tyr Ala Lys Ala Ile Asn Ala Gly Ser Lys Ser
130                 135                 140 cag gca ctt gac gta atc aaa gag tta gct cct agg gat tat gtt ctt         480
Gln Ala Leu Asp Val Ile Lys Glu Leu Ala Pro Arg Asp Tyr Val Leu
145                 150                 155                 160 cat ttc cat aac atc aac agc aat ttg gac aaa gtg ttc caa gtg cca         528
His Phe His Asn Ile Asn Ser Asn Leu Asp Lys Val Phe Gln Val Pro
                165                 170                 175 ccg gct cct tac gtt tca cct ttc tta agt tct tca ttt gat cag gtt         576
Pro Ala Pro Tyr Val Ser Pro Phe Leu Ser Ser Ser Phe Asp Gln Val
                180                 185                 190 cca gat gag ctt gag cat tgg gtg tcc gaa aac gtt atg gac gcc gca         624
Pro Asp Glu Leu Glu His Trp Val Ser Glu Asn Val Met Asp Ala Ala
            195                 200                 205 gcg cgt                                                                 630
Ala Arg
    210

<210> SEQ ID NO 3
<211> LENGTH: 210
<212> TYPE: PRT
<213> ORGANISM: Artificial
<220> FEATURE:
<223> OTHER INFORMATION: Synthetic Construct

<400> SEQUENCE: 3

Met Pro Arg Ser Gly Arg Phe Ser Ile Lys Ala Lys Asn Tyr Phe Leu
1               5                   10                  15

Thr Tyr Pro Lys Cys Asp Leu Thr Lys Glu Asn Ala Leu Ser Gln Ile
                20                  25                  30

Thr Asn Leu Gln Thr Pro Thr Asn Lys Leu Phe Ile Lys Ile Cys Arg
            35                  40                  45

Glu Leu His Glu Asn Gly Glu Pro His Leu His Ile Leu Ile Gln Phe
    50                  55                  60

Glu Gly Lys Tyr Asn Cys Thr Asn Gln Arg Phe Phe Asp Leu Val Ser
65                  70                  75                  80

Pro Thr Arg Ser Ala His Phe His Pro Asn Ile Gln Gly Ala Lys Ser
                85                  90                  95

Ser Ser Asp Val Lys Ser Tyr Ile Asp Lys Asp Gly Asp Val Leu Glu
            100                 105                 110

Trp Gly Thr Phe Gln Ile Asp Gly Arg Ser Ala Arg Gly Gly Gln Gln
    115                 120                 125

Thr Ala Asn Asp Ala Tyr Ala Lys Ala Ile Asn Ala Gly Ser Lys Ser
130                 135                 140

Gln Ala Leu Asp Val Ile Lys Glu Leu Ala Pro Arg Asp Tyr Val Leu
145                 150                 155                 160

His Phe His Asn Ile Asn Ser Asn Leu Asp Lys Val Phe Gln Val Pro
                165                 170                 175

Pro Ala Pro Tyr Val Ser Pro Phe Leu Ser Ser Ser Phe Asp Gln Val
                180                 185                 190

Pro Asp Glu Leu Glu His Trp Val Ser Glu Asn Val Met Asp Ala Ala
            195                 200                 205

Ala Arg
```

<210> SEQ ID NO 4
<211> LENGTH: 630
<212> TYPE: DNA
<213> ORGANISM: Artificial
<220> FEATURE:
<223> OTHER INFORMATION: TYLCSV Rep-210 modified sequence
<220> FEATURE:
<221> NAME/KEY: CDS
<222> LOCATION: (1)..(630)

<400> SEQUENCE: 4

| | | | | | | | | | | | | | | | | |
|---|---|---|---|---|---|---|---|---|---|---|---|---|---|---|---|---|
| atg | cct | aga | tcc | gga | agg | ttt | agc | atc | aaa | gct | aag | aat | tac | ttc | ttg | 48 |
| Met | Pro | Arg | Ser | Gly | Arg | Phe | Ser | Ile | Lys | Ala | Lys | Asn | Tyr | Phe | Leu | |
| 1 | | | | 5 | | | | | 10 | | | | | 15 | | |

| aca | tac | ccc | aag | tgt | gac | tta | act | aag | gag | aat | gca | ttg | tcc | cag | ata | 96 |
| Thr | Tyr | Pro | Lys | Cys | Asp | Leu | Thr | Lys | Glu | Asn | Ala | Leu | Ser | Gln | Ile | |
| | | | 20 | | | | | 25 | | | | | 30 | | | |

| act | aac | ttg | caa | act | ccc | act | aac | aag | ttg | ttc | att | aag | att | tgt | agg | 144 |
| Thr | Asn | Leu | Gln | Thr | Pro | Thr | Asn | Lys | Leu | Phe | Ile | Lys | Ile | Cys | Arg | |
| | | 35 | | | | | 40 | | | | | 45 | | | | |

| gaa | ctt | cac | gag | aat | gga | gaa | cca | cat | ctt | cat | atc | ttg | ata | cag | ttc | 192 |
| Glu | Leu | His | Glu | Asn | Gly | Glu | Pro | His | Leu | His | Ile | Leu | Ile | Gln | Phe | |
| 50 | | | | | 55 | | | | | 60 | | | | | | |

| gaa | ggc | aag | tat | aac | tgc | acc | aac | caa | cgt | ttc | ttt | gac | ctt | gtg | tcc | 240 |
| Glu | Gly | Lys | Tyr | Asn | Cys | Thr | Asn | Gln | Arg | Phe | Phe | Asp | Leu | Val | Ser | |
| 65 | | | | | 70 | | | | | 75 | | | | | 80 | |

| cct | acc | aga | tca | gcc | cat | ttt | cat | cca | aac | atc | cag | ggt | gct | aag | tcg | 288 |
| Pro | Thr | Arg | Ser | Ala | His | Phe | His | Pro | Asn | Ile | Gln | Gly | Ala | Lys | Ser | |
| | | | | 85 | | | | | 90 | | | | | 95 | | |

| agt | tca | gac | gtg | aag | tca | tac | att | gac | aaa | gac | ggg | gat | gtg | ctc | gag | 336 |
| Ser | Ser | Asp | Val | Lys | Ser | Tyr | Ile | Asp | Lys | Asp | Gly | Asp | Val | Leu | Glu | |
| | | | 100 | | | | | 105 | | | | | 110 | | | |

| tgg | gga | act | ttt | cag | ata | gac | ggt | cga | tcg | gct | aga | gga | ggt | cag | caa | 384 |
| Trp | Gly | Thr | Phe | Gln | Ile | Asp | Gly | Arg | Ser | Ala | Arg | Gly | Gly | Gln | Gln | |
| | | 115 | | | | | 120 | | | | | 125 | | | | |

| aca | gca | aac | gat | gca | tac | gct | aag | gct | atc | aac | gct | gga | tcc | aag | tca | 432 |
| Thr | Ala | Asn | Asp | Ala | Tyr | Ala | Lys | Ala | Ile | Asn | Ala | Gly | Ser | Lys | Ser | |
| 130 | | | | | 135 | | | | | 140 | | | | | | |

| cag | gca | ctt | gac | gta | atc | aaa | gag | tta | gct | cct | agg | gat | tat | gtt | ctt | 480 |
| Gln | Ala | Leu | Asp | Val | Ile | Lys | Glu | Leu | Ala | Pro | Arg | Asp | Tyr | Val | Leu | |
| 145 | | | | | 150 | | | | | 155 | | | | | 160 | |

| cat | ttc | cat | aac | atc | aac | agc | aat | ttg | gac | aaa | gtg | ttc | caa | gtg | cca | 528 |
| His | Phe | His | Asn | Ile | Asn | Ser | Asn | Leu | Asp | Lys | Val | Phe | Gln | Val | Pro | |
| | | | | 165 | | | | | 170 | | | | | 175 | | |

| ccg | gct | cct | tac | gtt | tca | cct | ttc | tta | agt | tct | tca | ttt | gat | cag | gtt | 576 |
| Pro | Ala | Pro | Tyr | Val | Ser | Pro | Phe | Leu | Ser | Ser | Ser | Phe | Asp | Gln | Val | |
| | | | 180 | | | | | 185 | | | | | 190 | | | |

| cca | gat | gag | ctt | gag | cat | tgg | gtg | tct | gaa | aac | gtt | atg | gac | gcc | gca | 624 |
| Pro | Asp | Glu | Leu | Glu | His | Trp | Val | Ser | Glu | Asn | Val | Met | Asp | Ala | Ala | |
| | | 195 | | | | | 200 | | | | | 205 | | | | |

| gcc | cgt | | | | | | | | | | | | | | | 630 |
| Ala | Arg | | | | | | | | | | | | | | | |
| | 210 | | | | | | | | | | | | | | | |

<210> SEQ ID NO 5
<211> LENGTH: 210
<212> TYPE: PRT
<213> ORGANISM: Artificial
<220> FEATURE:
<223> OTHER INFORMATION: Synthetic Construct -continued

```
<400> SEQUENCE: 5

Met Pro Arg Ser Gly Arg Phe Ser Ile Lys Ala Lys Asn Tyr Phe Leu
1               5                   10                  15

Thr Tyr Pro Lys Cys Asp Leu Thr Lys Glu Asn Ala Leu Ser Gln Ile
            20                  25                  30

Thr Asn Leu Gln Thr Pro Thr Asn Lys Leu Phe Ile Lys Ile Cys Arg
        35                  40                  45

Glu Leu His Glu Asn Gly Glu Pro His Leu His Ile Leu Ile Gln Phe
    50                  55                  60

Glu Gly Lys Tyr Asn Cys Thr Asn Gln Arg Phe Phe Asp Leu Val Ser
65                  70                  75                  80

Pro Thr Arg Ser Ala His Phe His Pro Asn Ile Gln Gly Ala Lys Ser
                85                  90                  95

Ser Ser Asp Val Lys Ser Tyr Ile Asp Lys Asp Gly Asp Val Leu Glu
            100                 105                 110

Trp Gly Thr Phe Gln Ile Asp Gly Arg Ser Ala Arg Gly Gly Gln Gln
        115                 120                 125

Thr Ala Asn Asp Ala Tyr Ala Lys Ala Ile Asn Ala Gly Ser Lys Ser
    130                 135                 140

Gln Ala Leu Asp Val Ile Lys Glu Leu Ala Pro Arg Asp Tyr Val Leu
145                 150                 155                 160

His Phe His Asn Ile Asn Ser Asn Leu Asp Lys Val Phe Gln Val Pro
                165                 170                 175

Pro Ala Pro Tyr Val Ser Pro Phe Leu Ser Ser Phe Asp Gln Val
            180                 185                 190

Pro Asp Glu Leu Glu His Trp Val Ser Glu Asn Val Met Asp Ala Ala
        195                 200                 205

Ala Arg
    210

<210> SEQ ID NO 6
<211> LENGTH: 774
<212> TYPE: DNA
<213> ORGANISM: Artificial
<220> FEATURE:
<223> OTHER INFORMATION: TYLCSV Coat Protein modified sequence
<220> FEATURE:
<221> NAME/KEY: CDS
<222> LOCATION: (1)..(774)

<400> SEQUENCE: 6 atg cca aag aga act ggt gat att cta atc tca act ccc gtg tct aag    48
Met Pro Lys Arg Thr Gly Asp Ile Leu Ile Ser Thr Pro Val Ser Lys
1               5                   10                  15 gtg cgt agg aga ctt aac ttt gac tct ccg tac acc tct cgt gca gct    96
Val Arg Arg Arg Leu Asn Phe Asp Ser Pro Tyr Thr Ser Arg Ala Ala
            20                  25                  30 gct ccc aca gtc cag ggc att aag agg cga tct tgg aca tac aga cct   144
Ala Pro Thr Val Gln Gly Ile Lys Arg Arg Ser Trp Thr Tyr Arg Pro
        35                  40                  45 atg tac agg aaa ccg agg atg tat agg atg tat cgt agc cca gat gtg   192
Met Tyr Arg Lys Pro Arg Met Tyr Arg Met Tyr Arg Ser Pro Asp Val
    50                  55                  60 cct cct ggt tgc gaa gga ccc tgc aag gtg caa tcg tat gag caa cgt   240
Pro Pro Gly Cys Glu Gly Pro Cys Lys Val Gln Ser Tyr Glu Gln Arg
65                  70                  75                  80 gac gat gtg aag cac acc gga gtt gtt cgt tgc gtt tct gat gtg act   288
Asp Asp Val Lys His Thr Gly Val Val Arg Cys Val Ser Asp Val Thr
```

```
                    85                  90                  95
aga ggt tca ggt atc act cac agg gtg gga aag cgt ttc tgt att aag      336
Arg Gly Ser Gly Ile Thr His Arg Val Gly Lys Arg Phe Cys Ile Lys
            100                 105                 110 tct att tac ata ttg ggt aag atc tgg atg gac gag aat atc aag aaa      384
Ser Ile Tyr Ile Leu Gly Lys Ile Trp Met Asp Glu Asn Ile Lys Lys
            115                 120                 125 cag aat cac act aat cag gtt atg ttc ttt ctt gtg cga gat cga aga      432
Gln Asn His Thr Asn Gln Val Met Phe Phe Leu Val Arg Asp Arg Arg
    130                 135                 140 cca tac gga acc agc cca atg gac ttc ggc cag gtg ttt aat atg ttc      480
Pro Tyr Gly Thr Ser Pro Met Asp Phe Gly Gln Val Phe Asn Met Phe
145                 150                 155                 160 gat aac gag cca tct act gca act gtg aaa aat gat ttg cgt gat aga      528
Asp Asn Glu Pro Ser Thr Ala Thr Val Lys Asn Asp Leu Arg Asp Arg
                165                 170                 175 tat cag gtg atg aga aag ttc cat gca acg gtg gtt ggt ggt cct tct      576
Tyr Gln Val Met Arg Lys Phe His Ala Thr Val Val Gly Gly Pro Ser
            180                 185                 190 gga atg aaa gag caa tgt ctt ctg aaa aga ttc ttt aag atc aac act      624
Gly Met Lys Glu Gln Cys Leu Leu Lys Arg Phe Phe Lys Ile Asn Thr
            195                 200                 205 cat gtc gtc tat aac cac cag gag caa gcg aaa tat gag aat cac act      672
His Val Val Tyr Asn His Gln Glu Gln Ala Lys Tyr Glu Asn His Thr
    210                 215                 220 gaa aat gct ttg ttg tta tac atg gcc tgt acc cac gca tct aat cca      720
Glu Asn Ala Leu Leu Leu Tyr Met Ala Cys Thr His Ala Ser Asn Pro
225                 230                 235                 240 gtt tac gca acg ctt aag atc cgt atc tat ttc tat gac gct gtg aca      768
Val Tyr Ala Thr Leu Lys Ile Arg Ile Tyr Phe Tyr Asp Ala Val Thr
                245                 250                 255 aac tag                                                              774
Asn

<210> SEQ ID NO 7
<211> LENGTH: 257
<212> TYPE: PRT
<213> ORGANISM: Artificial
<220> FEATURE:
<223> OTHER INFORMATION: Synthetic Construct

<400> SEQUENCE: 7

Met Pro Lys Arg Thr Gly Asp Ile Leu Ile Ser Thr Pro Val Ser Lys
1               5                   10                  15

Val Arg Arg Arg Leu Asn Phe Asp Ser Pro Tyr Thr Ser Arg Ala Ala
            20                  25                  30

Ala Pro Thr Val Gln Gly Ile Lys Arg Arg Ser Trp Thr Tyr Arg Pro
        35                  40                  45

Met Tyr Arg Lys Pro Arg Met Tyr Arg Met Tyr Arg Ser Pro Asp Val
    50                  55                  60

Pro Pro Gly Cys Glu Gly Pro Cys Lys Val Gln Ser Tyr Glu Gln Arg
65                  70                  75                  80

Asp Asp Val Lys His Thr Gly Val Val Arg Cys Val Ser Asp Val Thr
                85                  90                  95

Arg Gly Ser Gly Ile Thr His Arg Val Gly Lys Arg Phe Cys Ile Lys
            100                 105                 110

Ser Ile Tyr Ile Leu Gly Lys Ile Trp Met Asp Glu Asn Ile Lys Lys
            115                 120                 125
```

```
Gln Asn His Thr Asn Gln Val Met Phe Phe Leu Val Arg Asp Arg Arg
    130                 135                 140
Pro Tyr Gly Thr Ser Pro Met Asp Phe Gly Gln Val Phe Asn Met Phe
145                 150                 155                 160
Asp Asn Glu Pro Ser Thr Ala Thr Val Lys Asn Asp Leu Arg Asp Arg
                165                 170                 175
Tyr Gln Val Met Arg Lys Phe His Ala Thr Val Val Gly Gly Pro Ser
            180                 185                 190
Gly Met Lys Glu Gln Cys Leu Leu Lys Arg Phe Phe Lys Ile Asn Thr
        195                 200                 205
His Val Val Tyr Asn His Gln Glu Gln Ala Lys Tyr Glu Asn His Thr
    210                 215                 220
Glu Asn Ala Leu Leu Leu Tyr Met Ala Cys Thr His Ala Ser Asn Pro
225                 230                 235                 240
Val Tyr Ala Thr Leu Lys Ile Arg Ile Tyr Phe Tyr Asp Ala Val Thr
                245                 250                 255
Asn

<210> SEQ ID NO 8
<211> LENGTH: 447
<212> TYPE: DNA
<213> ORGANISM: Artificial
<220> FEATURE:
<223> OTHER INFORMATION: TYLCSV Rep 130 sequence
<220> FEATURE:
<221> NAME/KEY: CDS
<222> LOCATION: (51)..(443)
<220> FEATURE:
<221> NAME/KEY: misc_feature
<222> LOCATION: (231)..(231)
<223> OTHER INFORMATION: Point mutation from C (Rep-210 wild-type) to T
<220> FEATURE:
<221> NAME/KEY: misc_feature
<222> LOCATION: (233)..(233)
<223> OTHER INFORMATION: Point mutation from C (Rep 210 wild-type) to G

<400> SEQUENCE: 8
ggatccccct ggatactttg agtgtccccc gattcagaac gacagcaaaa atg cca         56
                                                       Met Pro
                                                         1 aga tca ggt cgt ttt agt atc aag gct aaa aat tat ttc ctt aca tat      104
Arg Ser Gly Arg Phe Ser Ile Lys Ala Lys Asn Tyr Phe Leu Thr Tyr
        5                   10                  15 ccc aaa tgt gat tta aca aaa gaa aat gca ctt tcc caa ata aca aac      152
Pro Lys Cys Asp Leu Thr Lys Glu Asn Ala Leu Ser Gln Ile Thr Asn
    20                  25                  30 cta caa aca ccc aca aac aaa tta ttc atc aaa att tgc aga gaa cta      200
Leu Gln Thr Pro Thr Asn Lys Leu Phe Ile Lys Ile Cys Arg Glu Leu
35                  40                  45                  50 cat gaa aat ggg gaa cct cat ctc cat att ttg atc caa ttc gaa gga      248
His Glu Asn Gly Glu Pro His Leu His Ile Leu Ile Gln Phe Glu Gly
                55                  60                  65 aaa tac aat tgt acc aat caa cga ttc ttc gac ctg gta tcc cca acc      296
Lys Tyr Asn Cys Thr Asn Gln Arg Phe Phe Asp Leu Val Ser Pro Thr
            70                  75                  80 agg tca gca cat ttc cat ccg aac att cag gga gct aaa tcg agc tcc      344
Arg Ser Ala His Phe His Pro Asn Ile Gln Gly Ala Lys Ser Ser Ser
        85                  90                  95 gac gtc aag tcc tat atc gac aag gac gga gat gtt ctt gaa tgg ggt      392
Asp Val Lys Ser Tyr Ile Asp Lys Asp Gly Asp Val Leu Glu Trp Gly
    100                 105                 110
```

```
act ttc cag atc gac gga cga tct gct agg gga gga caa cag aca gcc    440
Thr Phe Gln Ile Asp Gly Arg Ser Ala Arg Gly Gly Gln Gln Thr Ala
115                 120                 125                 130 tga attc                                                            447
```

<210> SEQ ID NO 9
<211> LENGTH: 130
<212> TYPE: PRT
<213> ORGANISM: Artificial
<220> FEATURE:
<223> OTHER INFORMATION: Synthetic Construct

<400> SEQUENCE: 9

```
Met Pro Arg Ser Gly Arg Phe Ser Ile Lys Ala Lys Asn Tyr Phe Leu
1               5                   10                  15

Thr Tyr Pro Lys Cys Asp Leu Thr Lys Glu Asn Ala Leu Ser Gln Ile
            20                  25                  30

Thr Asn Leu Gln Thr Pro Thr Asn Lys Leu Phe Ile Lys Ile Cys Arg
        35                  40                  45

Glu Leu His Glu Asn Gly Glu Pro His Leu His Ile Leu Ile Gln Phe
    50                  55                  60

Glu Gly Lys Tyr Asn Cys Thr Asn Gln Arg Phe Phe Asp Leu Val Ser
65                  70                  75                  80

Pro Thr Arg Ser Ala His Phe His Pro Asn Ile Gln Gly Ala Lys Ser
                85                  90                  95

Ser Ser Asp Val Lys Ser Tyr Ile Asp Lys Asp Gly Asp Val Leu Glu
            100                 105                 110

Trp Gly Thr Phe Gln Ile Asp Gly Arg Ser Ala Arg Gly Gly Gln Gln
        115                 120                 125

Thr Ala
    130
```

<210> SEQ ID NO 10
<211> LENGTH: 30
<212> TYPE: DNA
<213> ORGANISM: Artificial
<220> FEATURE:
<223> OTHER INFORMATION: Primer
<220> FEATURE:
<221> NAME/KEY: misc_feature
<222> LOCATION: (1)..(30)
<223> OTHER INFORMATION: Primer for PCR C4 mutagenesis

<400> SEQUENCE: 10
ctcatctcca tatttgatc caattcgaag                                     30

<210> SEQ ID NO 11
<211> LENGTH: 30
<212> TYPE: DNA
<213> ORGANISM: Artificial
<220> FEATURE:
<223> OTHER INFORMATION: Primer
<220> FEATURE:
<221> NAME/KEY: misc_feature
<222> LOCATION: (1)..(30)
<223> OTHER INFORMATION: Primer for PCR C4 mutagenesis

<400> SEQUENCE: 11
cttcgaattg gatcaaaata tggagatgag                                    30

<210> SEQ ID NO 12
<211> LENGTH: 774
<212> TYPE: DNA

-continued

```
<213> ORGANISM: Geminivirus TYLCSV

<400> SEQUENCE: 12
atgccgaagc gaaccggcga tatactaatt tcaacgcccg tctcgaaggt tcgtcgaaga      60
ctgaacttcg acagcccgta taccagccgt gctgctgccc ccactgtcca aggcatcaag     120
cgtcgatcat ggacttacag gcccatgtat cgaaagccgc ggatgtacag aatgtacaga    180
agccctgatg tacctccggg ttgtgaaggt ccctgtaaag tgcagtcgta cgagcagcgt    240
gatgacgtca agcataccgg tgttgtgcgt tgtgttagtg atgtaactag gggttctggt    300
attactcata gagttggtaa acgtttttgt atcaagtcaa tttatatatt aggaaagatt    360
tggatggatg aaaacataaa aaaacaaaat catactaacc aagtgatgtt tttccttgtt    420
cgagaccgaa ggccttatgg aactagtcct atggattttg gtcaagtttt taacatgttt    480
gataatgaac ccagtactgc tacggtgaag aacgacttac gggataggta tcaagtaatg    540
aggaagtttc atgctacggt tgttggaggt ccgtcaggga tgaaggagca gtgtttgctg    600
aagagatttt ttaaaattaa tacccatgta gtttataatc accaagagca ggcgaagtat    660
gaaaatcata ctgagaatgc cttgttattg tatatggctt gtactcatgc ttctaaccca    720
gtgtacgcta cgttgaaaat acgtatttat ttttatgatg ctgtaacaaa ttaa          774
```